(12) United States Patent
Park et al.

(10) Patent No.: US 10,421,767 B2
(45) Date of Patent: Sep. 24, 2019

(54) AMINOSILANE-FUNCTIONALIZED DIENES FOR USE IN FUNCTIONALIZATION OF ELASTOMERIC POLYMERS

(71) Applicant: Trinseo Europe GmbH, Horgen (CH)

(72) Inventors: Natja Park, Halle (DE); Michael Rossle, Merseburg (DE); Sven Thiele, Halle (DE); Daniel Heidenreich, Halle (DE); Benjamin Gutschank, Leipzig (DE)

(73) Assignee: TRINSEO EUROPE GMBH, Horgen (CH)

( * ) Notice: Subject to any disclaimer, the term of this patent is extended or adjusted under 35 U.S.C. 154(b) by 43 days.

(21) Appl. No.: 15/768,690

(22) PCT Filed: Oct. 17, 2016

(86) PCT No.: PCT/EP2016/074854
§ 371 (c)(1),
(2) Date: Apr. 16, 2018

(87) PCT Pub. No.: WO2017/067877
PCT Pub. Date: Apr. 27, 2017

(65) Prior Publication Data
US 2018/0291041 A1 Oct. 11, 2018

(30) Foreign Application Priority Data
Oct. 21, 2015 (EP) .................................... 15190827

(51) Int. Cl.
| | | |
|---|---|---|
| *C07F 7/10* | (2006.01) | |
| *C08F 230/08* | (2006.01) | |
| *C08F 236/10* | (2006.01) | |
| *C08L 43/04* | (2006.01) | |
| *B60C 1/00* | (2006.01) | |

(52) U.S. Cl.
CPC ............. *C07F 7/10* (2013.01); *C08F 230/08* (2013.01); *C08F 236/10* (2013.01); *C08L 43/04* (2013.01); *B60C 1/0016* (2013.01); *B60C 1/0025* (2013.01); *C08F 2230/085* (2013.01)

(58) Field of Classification Search
CPC ........................................................ C07F 7/10
See application file for complete search history.

(56) References Cited

U.S. PATENT DOCUMENTS

2010/0056712 A1* 3/2010 Oshima ................. C08F 236/04
524/572

\* cited by examiner

*Primary Examiner* — Arrie L Reuther
(74) *Attorney, Agent, or Firm* — Barnes & Thornburg LLP; G. Peter Nichols

(57) ABSTRACT

The present invention relates to novel aminosilane-functionalized diene compounds of the following Formula I:

Formula I wherein
each R' is independently selected from $C_1$-$C_{12}$ alkyl, $C_6$-$C_{18}$ aryl, $C_7$-$C_{18}$ alkylaryl, tri($C_1$-$C_6$ alkyl, $C_6$-$C_{12}$ aryl or $C_7$-$C_{18}$ alkylaryl)silyl and allyl, wherein two R' groups may be connected to form a ring and the ring may contain, further to the Si-bonded nitrogen atom, one or more of an oxygen atom, a nitrogen atom, an >N($C_1$-$C_6$ alkyl or $C_7$-$C_{18}$ alkylaryl) group and a sulfur atom;
each R" is independently selected from $C_1$-$C_6$ hydrocarbyl;
$R_a$, $R_b$, $R_c$, $R_d$ and $R_e$ are independently selected from hydrogen, methyl and ethyl;
x is an integer selected from 0, 1 and 2, y is an integer selected from 1, 2 and 3 and x+y=3.

The diene compounds are useful as modifying monomers in the polymerization of conjugated diene monomers.

20 Claims, No Drawings

AMINOSILANE-FUNCTIONALIZED DIENES FOR USE IN FUNCTIONALIZATION OF ELASTOMERIC POLYMERS

This application claims priority to International Application No. PCT/EP2016/074854 filed Oct. 17, 2016 and to European Application No. 15190827.4 filed Oct. 21, 2015; the entire contents of each are incorporated herein by reference.

FIELD OF THE INVENTION

The present invention is directed to novel diene compounds which are useful as modifying monomers in the polymerization of conjugated diene monomers, optionally together with aromatic vinyl monomers, thus producing polymers, specifically elastomeric polymers, which can favorably be used in rubber articles such as tires.

BACKGROUND OF THE INVENTION

Increasing oil prices and national legislation requiring the reduction of automotive carbon dioxide emissions force tire and rubber producers to produce "fuel-efficient" and thus fuel-saving tires. One approach for obtaining fuel-efficient tires lies in the production of tire formulations having reduced hysteresis loss. The hysteresis loss of a cross-linked elastomeric polymer composition is related to its tan δ value at 60° C. (see ISO 4664-1:2005; Rubber, Vulcanized or thermoplastic; Determination of dynamic properties—part 1: General guidance).

Vulcanized elastomeric polymer compositions having relatively low tan δ values at 60° C. are generally preferred for having lower hysteresis loss. In the final tire product, this translates into a lower rolling resistance and better fuel economy. In contrast, a lower tan δ value at 0° C. corresponds to a deteriorated wet grip of the tire product. Thus, it is generally accepted that a lower rolling resistance tire can be made at the expense of deteriorated wet grip properties. For example, if, in a random solution styrene-butadiene rubber (random SSBR), the polystyrene unit concentration is reduced with respect to the total polybutadiene unit concentration, the SSBR glass transition temperature is reduced and, as a result, both tan δ at 60° C. and tan δ at 0° C. are reduced, generally corresponding to improved rolling resistance and deteriorated wet grip performance of the tire. Accordingly, when assessing the rubber vulcanizate performance correctly, both tan δ at 60° C. and tan δ at 0° C. should be monitored along with the tire heat build-up.

WO 2012/091753 (Bridgestone Corp.) relates to silane-functionalized polymers and rubber vulcanizates prepared therefrom. The authors describe the use of certain alkenylaminosilanes for use in the initiation of anionic polymerizations.

US 2010/0056712 (Sumitomo Chemical Co.) relates to a conjugated diene polymer obtained by polymerizing a conjugated diene monomer and a vinylaminosilane in the presence of an alkali metal catalyst.

WO 2011/028523 (Bridgestone Corp.) relates to a process for preparing a polydiene, the process comprising the polymerization of a conjugated diene monomer with a lanthanide-based catalyst system in the presence of a vinylsilane, an allylsilane or an allylvinylsilane.

WO 2015/055252 (Trinseo Europe GmbH) relates to vinylsilane compounds which are useful as modifying monomers in the polymerization of conjugated diene monomers such as 1,3-butadiene, optionally together with an aromatic vinyl monomer such as styrene.

The present invention aims the provision of cured elastomeric polymer (rubber) compositions and means to provide such compositions, where the compositions exhibit improved tan δ values, corresponding to an improved balance of rolling resistance and wet grip performance.

SUMMARY OF THE INVENTION

The present invention is inter alia based on the finding that the above objects can be solved by carrying out the polymerization of conjugated diene monomers such as 1,3-butadiene ("butadiene") and isoprene in the presence of a specific aminosilane-functionalized diene compound.

Thus, in a first aspect, the present invention provides a diene compound of the following Formula 1:

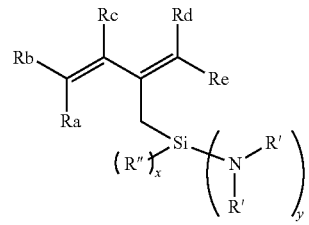

Formula 1 wherein
each R' is independently selected from $C_1$-$C_{12}$ alkyl, $C_6$-$C_{18}$ aryl, $C_7$-$C_{18}$ alkylaryl, tri($C_1$-$C_6$ alkyl, $C_6$-$C_{12}$ aryl or $C_7$-$C_{18}$ alkylaryl)silyl and allyl, wherein two R' groups may be connected to form a ring and the ring may contain, further to the Si-bonded nitrogen atom, one or more of an oxygen atom, a nitrogen atom, an >N($C_1$-$C_6$ alkyl or $C_7$-$C_{18}$ alkylaryl) group and a sulfur atom;
each R" is independently selected from $C_1$-$C_6$ hydrocarbyl;
$R_a$, $R_b$, $R_c$, $R_d$ and $R_e$ are independently selected from hydrogen, methyl and ethyl;
x is an integer selected from 0, 1 and 2, y is an integer selected from 1, 2 and 3 and x+y=3.

In a second aspect, the present invention provides a process for preparing the diene compound of Formula 1 of the first aspect of the invention, said process comprising reacting a compound of Formula 2 and a compound of Formula 3 in the presence of (i) a metal selected from the group including magnesium, zinc, aluminum and boron and (ii) a transition metal catalyst in a solvent:

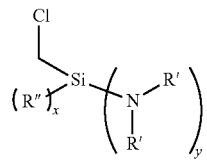

Formula 2

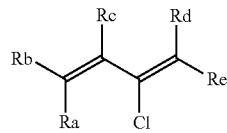

Formula 3 wherein $R_a$, $R_b$, $R_c$, $R_d$, $R_e$ R', R", x and y are as defined in the first aspect of the invention, generally and in any embodiment thereof.

In a third aspect, the present invention provides a process for preparing an elastomeric polymer, said process comprising the step of polymerizing at least one conjugated diene monomer, a diene compound of Formula 1 as defined in the first aspect of the invention and optionally one or more aromatic vinyl monomers in the presence of an initiator compound or a catalyst to form a living elastomeric polymer.

In a fourth aspect, the present invention provides an elastomeric polymer obtainable by polymerizing at least one conjugated diene monomer, a diene compound of Formula 1 as defined in the first aspect of the invention and optionally one or more aromatic vinyl monomers in the presence of an initiator compound or a catalyst.

In a fifth aspect, the present invention provides a non-cured polymer composition comprising the elastomeric polymer as defined in the fourth aspect of the invention and one or more further components selected from (i) components which are added to or formed as a result of the polymerization process used for making said polymer, (ii) components which remain after solvent removal from the polymerization process and (iii) components which are added to the polymer after completion of the polymer manufacturing process, thus including components which are added to the "solvent-free" polymer by application of (but not limited to) a mechanical mixer.

In a sixth aspect, the present invention provides a vulcanized polymer composition which is obtained by vulcanizing a non-cured polymer composition of the invention which comprises one or more vulcanizing agents.

In a seventh aspect, the present invention provides a method of making a vulcanized polymer composition, comprising the step of vulcanizing a non-cured polymer composition of the invention which comprises one or more vulcanizing agents.

In an eighth aspect, the present invention provides an article comprising at least one component formed from the vulcanized polymer composition of the invention.

It has been found that a significant improvement in the rolling resistance and wet grip can be accomplished by making use of the aminosilane-functionalized diene compound of the invention as a backbone modifier for making an elastomeric polymer, in particular SSBR, PBR, PIR, SSIR and SSIBR, more particularly SSBR and PBR, including high-cis and low-cis BR, such as high-cis BR produced by using an Nd catalyst. For example, a cured (vulcanized) SSBR of the invention exhibits an excellent or improved balance of tan δ at 0° C. and tan δ at 60° C., reflecting a better balance of low rolling resistance and high wet grip, as compared to an SSBR not being based on the diene compound of the invention. Moreover, the cured rubber, especially the cured SSBR, exhibits acceptable or even improved processing properties, such as an acceptable Mooney (CML1-4) viscosity.

DETAILED DESCRIPTION

Aminosilane-Functionalized Diene Compound of Formula 1

The diene compound of Formula 1 of the first aspect of the invention is characterized by being substituted in position 2 of the diene structure with an aminosilyl group, bonded via a methylene (—$CH_2$—) group.

In the diene compound of Formula 1, each R' is preferably independently selected from methyl, ethyl, n-butyl, n-hexyl, n-octyl, cyclohexyl and benzyl.

In one embodiment, the two R' groups are connected to form, together with the Si-bonded nitrogen atom, a 5- to 12-membered ring, such as a cyclohexylamine group, a cycloheptylamino group, a cyclooctylamino group, a cyclododecylamino group or a cyclopentylamino group, preferably a 5- to 8-membered ring. In another embodiment, y is 1 and the group —(NR'R')$_y$ is represented by piperazine, optionally substituted at the nitrogen atom in position 4 with $C_1$-$C_6$ alkyl or $C_7$-$C_{18}$ alkylaryl, piperidine or morpholine. In another embodiment, the two R' groups are each an ethyl group, which are again connected via an oxygen atom, thus forming a morpholine ring with the Si-bonded nitrogen atom.

The $C_1$-$C_6$ hydrocarbyl group for R" includes $C_1$-$C_6$ alkyl and phenyl. It is preferably methyl.

In a preferred embodiment, x and y are each 1.

$R_a$, $R_b$, $R_c$, $R_d$ and $R_e$ are preferably identical and more preferably are each hydrogen.

In one embodiment, $R_a$, $R_b$, $R_c$, $R_d$ and $R_e$ are each hydrogen and x and y are independently integers selected from 1 and 2 (and all other substituents of Formula 1 are as defined above or in other embodiments defined herein).

In specific embodiments, the diene compound of Formula 1 is represented by the following compounds:

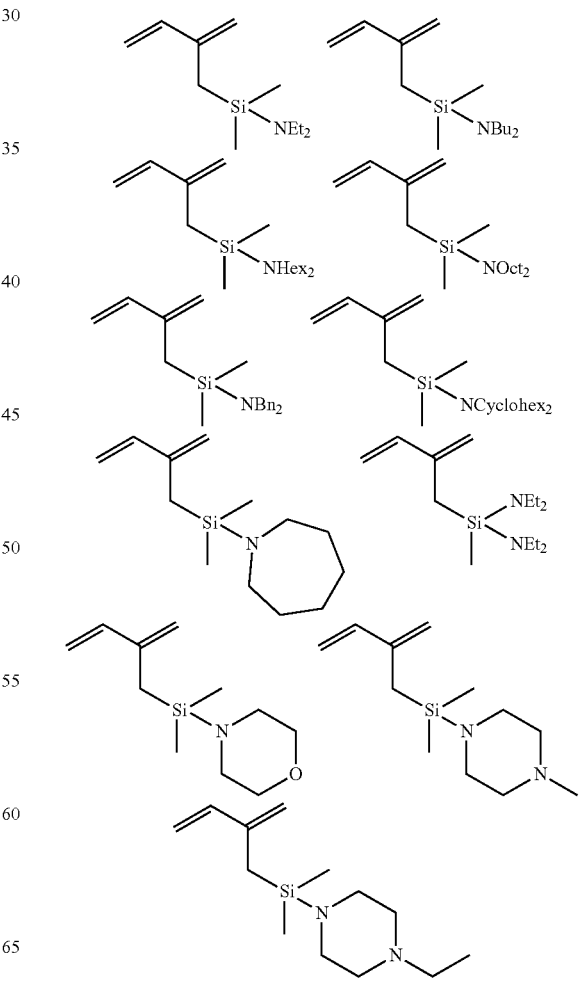

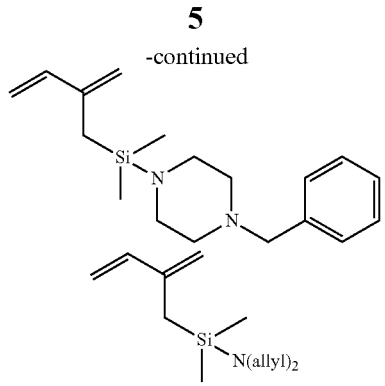

Preparation of the Aminosilane-Functionalized Diene Compound of Formula 1

According to the second aspect of the invention, the diene compound of Formula 1 can be prepared by reacting a compound of Formula 2 and a compound of Formula 3 in the presence of (i) a metal selected from the group consisting of magnesium, zinc, aluminum and boron and (ii) a transition metal catalyst in a solvent.

In the compound of Formula 2, the meaning of R', R", x and y is identical to that for the diene compound of Formula 1, including any embodiment thereof, as defined above. Compounds of Formula 2, wherein R" is methyl, y is 1 and the group —(NR'R')$_y$ is represented by piperazine, optionally substituted at the nitrogen atom in position 4 with $C_1$-$C_6$ alkyl or $C_7$-$C_{18}$ alkylaryl, piperidine or morpholine, are believed to be novel compounds. They can be prepared by reacting a (chloromethyl)silane with a corresponding amine HNR'$_2$.

The compound of Formula 3 is chloroprene or a chloroprene derivative and is preferably chloroprene.

In one embodiment the transition metal catalyst is based on nickel, palladium, platinum, iron or other group-VIII metals with ligands. In one preferred embodiment, the general formula for a nickel containing catalyst is ML$_2$X$_2$, wherein M is nickel, L is a phosphine containing ligand and X is a halogen. Preferred transition metal catalysts are nickel catalysts with ligands such as bis(diphenylphosphine)propane nickel (II) dichloride, bis(diphenylphosphine)ethane nickel (II) dichloride, 1,1'-bis(diphenylphosphino)ferrocene dichloro nickel (II) acetylacetonate chloride or palladium catalysts with ligands, such as tetrakis(triphenylphosphine) palladium (0) or bis(dibenzylideneacetone)palladium (0). Preferably used are bis(diphenylphosphine)-propane nickel (II) dichloride, bis(diphenylphosphine)ethane nickel (II) dichloride and tetrakis(triphenylphosphine)palladium (0). Most preferably used is bis(diphenylphosphine)-propane nickel (II) dichloride. The catalyst can be used in an amount of 0.01 to 20 mol %, preferably 0.1 to 10 mol % and more preferably 0.2 to 5 mol %, based on the amount of compound of Formula 3.

In one embodiment, the metal used in the process is magnesium, zinc, boron or aluminium, preferably magnesium or zinc and most preferably magnesium to form a Grignard reagent. For catalyzing the Grignard reaction, a catalytic amount of, e.g., dibromoethane, zinc chloride (ZnCl$_2$), iodine (I$_2$) or benzylchloride may be added in the reaction. When the metal used in the process of the second aspect is magnesium, the reaction generally is a Grignard reaction of a (chloromethyl)aminosilane of Formula 2 with chloroprene or a chloroprene derivative of Formula 3 in presence of a catalytic system. The preparation of (chloromethyl)dimethylaminosilane is described, e.g., in WO 2014/040640. In one embodiment, the process of the second aspect of the invention comprises the steps of (i) reacting the compound of Formula 2 with magnesium in a solvent to form a Grignard reagent and (ii) reacting said Grignard reagent with the compound of Formula 3 in the presence of a nickel catalyst. Preferably, the molar ratio of the Grignard reagent to chloroprene is 0.95 to 3 equivalents, preferably 1.0 to 2 equivalents and more preferably 1.01 to 1.5 equivalents. The reaction can be carried out under conditions as they will be apparent to a person skilled in the art.

In one embodiment, the molar ratio of the metal to the compound of Formula 2 is 0.95 to 3 equivalents, preferably 1.0 to 2 equivalents and more preferably 1.01 to 1.5 equivalents.

In another embodiment, the solvent is an ether or thioether, for example selected from tetrahydrofuran (THF), diethyl ether, 2-methyltetrahydrofuran, tert-butyl methyl ether, dioxane, cyclopentyl methyl ether and a mixture of two or more thereof, preferably tetrahydrofuran. The total concentration of the reactants in the solvent is usually in the range from 0.1 to 2.0 M.

Generally, the preparation of (2-methylene-but-3-enyl) silanes is described in US 2013/196019 (corresponding to WO 2011/116223), the content of which is incorporated herein by reference in its entirety. The diene compounds of Formula 1 of the present invention are distinguished from the silanes prepared in US 2013/196019 in that the silyl group additional carries an amino substituent, but can generally be prepared in a corresponding manner.

Polymerization

The process for preparing the elastomeric polymer according to the third aspect of the present invention comprises the step of polymerizing at least one conjugated diene monomer, a diene compound of Formula 1 as defined in the first aspect of the invention, or in any embodiment thereof, and optionally one or more aromatic vinyl monomers in the presence of an initiator compound or a catalyst to form a living elastomeric polymer. The elastomeric polymer can be prepared generally via anionic, radical or transition metal-catalyzed polymerization. In one preferred embodiment, the elastomeric polymer is prepared by anionic polymerization. In another preferred embodiment, the elastomeric polymer is prepared by transition metal-catalyzed polymerization. The elastomeric polymer can be prepared in a batch, continuous or semi-batch polymerization process. Two or more diene compounds of Formula 1 may be used in combination. The polymerization may be conducted in a solvent and may be carried out with one or more of chain end-modifying agents, coupling agents including modified coupling agents, randomizer compounds and polymerization accelerator compounds.

In one embodiment, the amount of the diene compound of Formula 1 is from 0.01 to 50 wt. %, preferably from 0.02 to 20 wt. %, more preferably from 0.04 to 10 wt. %, even more preferably from 0.05 to 5 wt. %, based on the total amount of polymerizable monomers.

Further to the following specific disclosure, generally applicable directions on polymerization technologies including polymerization initiator compounds, polar coordinator compounds and accelerators (for increasing/changing the reactivity of the initiator, for randomly arranging aromatic vinyl monomers and/or for randomly arranging and/or changing the concentration of 1,2-polybutadiene or 1,2-polyisoprene or 3,4-polyisoprene units introduced in the polymer); the amounts of each compound; monomer(s); and suitable process conditions are described in US 2011/

082253 (corresponding to WO 2009/148932), the content of which is incorporated herein by reference in its entirety.

Conjugated Diene Monomers

The at least one conjugated diene monomer used in the process of the third aspect of the invention is a monomer which is different from and not within the scope of the diene compound of Formula 1. Exemplary conjugated diene monomers useful in the present invention include 1,3-butadiene, 2-($C_1$-$C_5$ alkyl)-1,3-butadiene such as isoprene (2-methyl-1,3-butadiene), 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene and 1,3-cyclooctadiene and 2-($C_2$-$C_8$ alkenyl)-1,3-butadiene such as for example myrcene or farnesene. A mixture of two or more conjugated dienes may be used. Preferred conjugated dienes include 1,3-butadiene and isoprene. In one embodiment, the conjugated diene is 1,3-butadiene.

Aromatic Vinyl Monomers

The optional aromatic vinyl monomers include monovinylaromatic compounds, i.e. compounds having only one vinyl group attached to an aromatic group, and di- or higher vinylaromatic compounds which have two or more vinyl groups attached to an aromatic group. Exemplary aromatic vinyl monomers optionally used together with the at least one conjugated diene include styrene, $C_{1-4}$ alkyl-substituted styrene such as 2-methylstyrene, 3-methylstyrene, 4-methylstyrene, 2,4-dimethylstyrene, 2,4,6-trimethylstyrene, α-methylstyrene, 2,4-diisopropylstyrene and 4-tert-butylstyrene, stilbene, vinyl benzyl dimethylamine, (4-vinylbenzyl) dimethyl aminoethyl ether, N,N-dimethylaminoethyl styrene, tert-butoxystyrene, vinylpyridine and divinylaromatic compounds such as 1,2-divinylbenzene, 1,3-divinylbenzene and 1,4-divinylbenzene. Two or more aromatic vinyl monomers may be used in combination. A preferred aromatic vinyl monomer is a monovinylaromatic compound, more preferably styrene. The monovinylaromatic compound(s) may be used, depending on the application, in total amounts of 40-70 wt. %, or 15-40 wt. %, or 2-15 wt. %, based on the total weight of monomers used in the polymerization reaction. The di- or higher vinylaromatic compounds such as divinylbenzene, including 1,2-divinylbenzene, 1,3-divinylbenzene and 1,4-divinylbenzene, may be used in a total amount of 1 wt. % or less (based on the total molar weight of the monomers used to make the polymer). In one preferred embodiment, 1,2-divinylbenzene is used in combination with one or more selected from styrene, butadiene and isoprene, thus forming, e.g., SBR (styrene butadiene rubber), BR (butadiene rubber), IR (isoprene rubber), ISBR (isoprene styrene butadiene rubber) or SIR (styrene isoprene rubber).

Other Monomers

Comonomers other than the diene compound of Formula 1, the conjugated diene monomer and the aromatic vinyl monomer, which may be used in preparing the elastomeric polymer of the invention, include acrylic monomers such as acrylonitrile, acrylates, e.g., acrylic acid, methyl acrylate, ethyl acrylate, propyl acrylate and butyl acrylate, and methacrylates, e.g., methyl methacrylate, ethyl methacrylate, propyl methacrylate and butyl methacrylate.

Initiator Compounds

In one embodiment of the third aspect of the invention, an initiator compound is used in the polymerization. Two or more initiator compounds may be used in combination. The initiator compound may be a monovalent or multivalent (divalent, trivalent, etc.) initiator compound. Suitable initiator compounds include alkali metals, organoalkali metal compounds, a complex between an alkali metal and a polar compound, an oligomer containing an alkali metal, and Lewis acid-base complexes. Exemplary alkali metals include lithium, sodium, potassium, rubidium and cesium. Exemplary organoalkali metal compounds include ethyllithium, n-butyllithium, s-butyllithium, t-octyllithium, isopropyllithium, phenyllithium, cyclohexyllithium, 2-butyllithium, 4-phenylbutyllithium, t-butyldimethylsilyloxypropyllithium, dialkylaminopropyllithium, N-morpholinopropyl lithium, lithiumdiisopropylamide, lithium piperidide, lithium pyrrolidide, dilithiated diphenylethylene compounds, multi-lithiated trivinyl benzene compounds, sodium biphenylide, sodium naphthalenide and potassium naphthalenide. Exemplary complexes between an alkali metal and a polar compound include a lithium-tetramethylethylenediamine complex, a lithium-tetrahydrofuran complex, a lithium-ditetrahydrofuranepropane complex, and the sodium and potassium analogues thereof. More preferably, the initiator compound is a mono- or dilithium alkyl, alkylaryl or aryl compound. Further useful initiators include the amino silane polymerization initiators described in WO 2014/040640 and the polymerization initiators described in WO 2015/010710, the content of which is incorporated herein by reference in its entirety. The total amount of the initiator(s), in particular the organolithium initiator(s), will be adjusted depending on the monomer and target molecular weight. The total amount is typically from 0.05 to 5 mmol, preferably from 0.2 to 3 mmol per 100 grams of polymerizable monomers.

Generally, organolithium initiators may be used for the production of SSBR or low-cis BR.

Catalyst

In another embodiment of the third aspect of the invention, a catalyst is used in the polymerization. Two or more catalysts may be used in combination. Generally, the catalyst contains one or more selected from nickel, cobalt, titanium and rare earth elements having an atomic number of 57 to 71 in the periodic table. The catalyst preferably contains one or more rare earth elements having an atomic number of 57 to 71 in the periodic table. The rare earth element is more preferably selected from La, Pr, Nd, Gd and Dy and is most preferably Nd.

The catalyst is usually in the form of a catalyst composition which is prepared by mixing and optionally reacting at least one rare earth element compound and at least one activator compound. Preferably, the rare earth element compound is a carboxylate, alcoholate, amide or hydrocarbyl compound of a rare earth element, in particular a neodymium carboxylate, more preferably selected from neodymium versatate, neodymium neodecanoate and a combination thereof. The activator compound can be a Lewis acid, including halogenated boron compounds, halogenated aluminum compounds, alkyl aluminum halides and alumoxanes, such as for example methylalumoxane.

Useful catalysts for the third aspect of the present invention, including rare earth element compounds and activators, are disclosed in US 2005/090383 (corresponding to WO 2003/033545), the content of which is incorporated herein by reference in its entirety.

Generally, rare earth element catalysts may be used for the production of high-cis BR.

In one embodiment, the polymerization process can be performed in a solvent as a slurry or solution polymerization. In another embodiment, the polymerization process can be performed as mass polymerization in the gas phase or in the essential absence of a solvent.

Solvent

The polymerization is usually conducted as a solution polymerization, wherein the formed polymer is substantially soluble in the reaction mixture, or as a suspension/slurry polymerization, wherein the formed polymer is substantially insoluble in the reaction medium. More preferably, the polymer is obtained in a solution polymerization. As the polymerization solvent, a hydrocarbon solvent is conventionally used which does not deactivate the initiator, catalyst or active polymer chain. The polymerization solvent may be a combination of two or more solvents. Exemplary hydrocarbon solvents include aliphatic and aromatic solvents. Specific examples include (including all conceivable constitutional isomers): propane, butane, pentane, hexane, heptane, butene, cyclohexane, propene, pentene, hexane, octane, benzene, toluene, ethylbenzene and xylene.

Chain End-Modifying Agents

One or more chain end-modifying agents may be used in the polymerization reaction of the present invention for further controlling polymer properties by reacting with the terminal ends of the polymer chains in the polymer of the invention. Generally, silane-sulfide omega chain end-modifying agents such as disclosed in WO 2007/047943, WO 2009/148932, U.S. Pat. No. 6,229,036 and US 2013/0131263, the content of which is incorporated herein by reference in its entirety, can be used for this purpose. Other chain end-modifying agents suitable for use in the present invention are those disclosed in WO2014/040640 and WO2015/010710 and the silane sulfide modifiers described in WO2014/040639.

The chain end-modifying agents may be added intermittently (at regular or irregular intervals) or continuously during the polymerization, but are preferably added at a conversion rate of the polymerization of more than 80 percent and more preferably at a conversion rate of more than 90 percent. Preferably, a substantial amount of the polymer chain ends is not terminated prior to the reaction with the chain end-modifying agent; that is, living polymer chain ends are present and are capable of reacting with the modifying agent.

Coupling Agents

For further controlling polymer molecular weight and polymer properties, a coupling agent ("linking agent") can be used as an optional component in the process of the invention. A coupling agent will reduce hysteresis loss by reducing the number of free chain ends of the elastomeric polymer and/or reduce the polymer solution viscosity, compared with non-coupled essentially linear polymer macromolecules of identical molecular weight. Coupling agents such as tin tetrachloride may functionalize the polymer chain end and react with components of an elastomeric composition, for example with a filler or with unsaturated portions of a polymer. Exemplary coupling agents are described in U.S. Pat. No. 3,281,383, 3,244,664 and 3,692, 874 (e.g., tetrachlorosilane); U.S. Pat. Nos. 3,978,103, 4,048,206, 4,474,908 and 6,777,569 (blocked mercaptosilanes); U.S. Pat. No. 3,078,254 (multi-halogen-substituted hydrocarbon, such as 1,3,5-tri(bromo methyl) benzene); U.S. Pat. No. 4,616,069 (tin compound and organic amino or amine compound); and U.S. 2005/0124740. In one embodiment, preferred coupling agents are silicon tetrachloride, tin tetrachloride and tetramethoxysilane. Generally, the chain end-modifying agent is added before, during or after the addition of the coupling agent, and the modification reaction is preferably carried out after the addition of the coupling agent. The total amount of coupling agents used will influence the Mooney viscosity of the coupled polymer and is typically in the range of from 0.001 to 4.5 milliequivalents per 100 grams of the elastomeric polymer, for example 0.01 to about 1.5 milliequivalents per 100 grams of polymer.

Randomizer Compounds

Randomizer compounds as conventionally known in the art (also known as polar coordinator compounds) may optionally be added to the monomer mixture or polymerization reaction, in order to adjust the microstructure (i.e. the content of vinyl bonds) of the conjugated diene part of the polymer, or to adjust the composition distribution of any aromatic vinyl monomer and of the vinyl bonds in the polymer chain. A combination of two or more randomizer compounds may be used. Randomizer compounds useful in the invention are generally exemplified by Lewis base compounds. Suitable Lewis bases for use in the present invention are, for example, ether compounds such as diethyl ether, di-n-butyl ether, ethylene glycol diethyl ether, ethylene glycol dibutyl ether, diethylene glycol dimethyl ether, propylene glycol dimethyl ether, propylene glycol diethyl ether, propylene glycol dibutyl ether, ($C_1$-$C_8$ alkyl)tetrahydrofurylethers (including methyltetrahydrofurylether, ethyltetrahydrofurylether, propyltetrahydrofurylether, butyltetrahydrofurylether, hexyltetrahydrofurylether and octyltetrahydrofurylether), tetrahydrofuran, 2,2-(bistetrahydrofurfuryl)propane, bistetrahydrofurfurylformal, methyl ether of tetrahydrofurfuryl alcohol, ethyl ether of tetrahydrofurfuryl alcohol, butyl ether of tetrahydrofurfuryl alcohol, ol-methoxytetrahydrofuran, dimethoxybenzene and dimethoxyethane, and tertiary amines such as triethylamine, pyridine, N,N,N',N'-tetramethyl ethylenediamine, dipiperidinoethane, methyl ether of N,N-diethylethanolamine, ethyl ether of N,N-diethylethanolamine, N,N-diethylethanolamine and dimethyl N,N-tetrahydrofurfuryl amine. Examples of preferred randomizer compounds are identified in WO 2009/148932, the content of which is incorporated herein by reference in its entirety. The randomizer compound will typically be added at a molar ratio of randomizer compound to initiator compound of from 0.012:1 to 10:1, preferably from 0.1:1 to 8:1 and more preferably from 0.25:1 to about 6:1.

Accelerator Compounds

The polymerization can optionally include accelerators to increase the reactivity of the initiator (and, thus, to increase the polymerization rate), to randomly arrange aromatic vinyl monomers introduced into the polymer, or to provide a single chain of aromatic vinyl monomers, thus influencing the distribution of aromatic vinyl monomers in a living anionic elastomeric copolymer. Examples of accelerators include sodium alkoxides or sodium phenoxides and potassium alkoxides or potassium phenoxides, preferably potassium alkoxides or potassium phenoxides, such as potassium isopropoxide, potassium t-butoxide, potassium t-amyloxide, potassium n-heptyloxide, potassium benzyloxide, potassium phenoxide; potassium salts of carboxylic acids, such as isovaleric acid, caprylic acid, lauric acid, palmitic acid, stearic acid, oleic acid, linolenic acid, benzoic acid, phthalic acid and 2-ethyl hexanoic acid; potassium salts of organic sulfonic acids, such as dodecyl benzenesulfonic acid, tetradecyl benzenesulfonic acid, hexadecyl benzenesulfonic acid and octadecyl benzenesulfonic acid; and potassium salts of organic phosphorous acids, such as diethyl phosphite, diisopropyl phosphite, diphenyl phosphite, dibutyl phosphite, and dilauryl phosphite. Such accelerator compounds may be added in a total amount of from 0.005 to 0.5 mol per 1.0 gram atom equivalent of lithium initiator. If less than 0.005 mol is added, a sufficient effect is not typically achieved. On the other hand, if the amount of the accelerator compound is more than about 0.5 mol, the productivity and efficiency of the chain end modification reaction can be significantly reduced.

Dosing

The diene compound of Formula 1 can be used in an amount of from 0.1 equivalent, preferably from 0.4 equivalent per equivalent of initiator compound(s) to 50 wt. % based on the total amount of the resulting elastomeric polymer. When the polymer of the invention is used in tire applications, for example in a rubber compound for a tire tread or tire sidewall, it is preferable to use the diene compound of Formula 1 in an amount of from 0.1 equivalent, preferably from 0.4 equivalent per equivalent of initiator compound(s) to 20 wt. %, more preferably up to 10 wt. %, even more preferably up to 5 wt. % based on the elastomeric polymer. The remaining amount of the elastomeric polymer is derived from the conjugated diene monomer and optional aromatic vinyl monomer as well as further optional components, such as chain end-modifying agents, coupling agents and randomizers.

In a catalytic polymerization process, any amount of the diene compound of Formula 1 can be used ranging from an amount of from 0.00005 wt. %, preferably from 0.0001 wt. % to 50 wt. %, based on the total amount of the resulting elastomeric polymer. When the polymer of the invention is used in tire applications, for example in a rubber compound for a tire tread or tire sidewall, it is preferable to use the diene compound of Formula 1 in an amount of from 0.0001 to 20 wt. %, more preferably up to 10 wt. %, even more preferably up to 5 wt. % based on the elastomeric polymer.

The mode of addition ("dosing") of the diene compound of Formula 1 in the polymerization process relative to the conjugated diene monomer and optional aromatic vinyl monomer, initiator compound and other components will affect the structure of the resulting polymer. The diene compound of Formula 1 can be added to the polymerization mixture at any time, e.g. prior to the start of the polymerization process, during the polymerization process or after completion of the polymerization process, but prior to chain-end termination. Thus, statistical copolymers and block copolymers having blocks of diene compound polymer and blocks of other monomers in desired proportions and sequences can be prepared. For example, the following polymer structures could be envisaged for adjusting polymer properties (without intending any limitation on dosing options generally available):

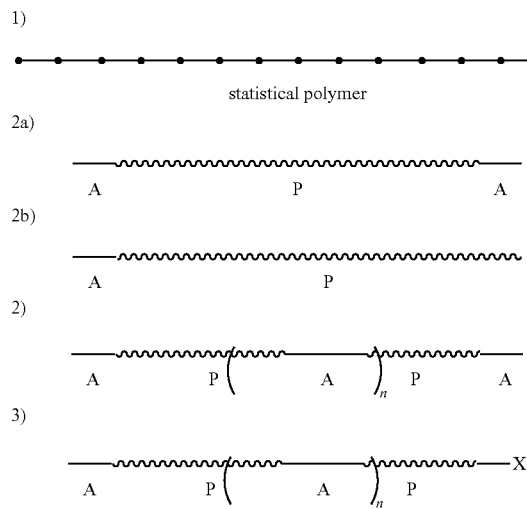

-continued

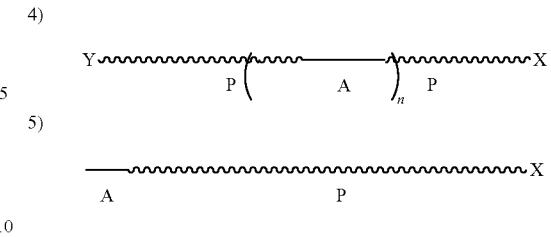

A: block of polymer of diene compound of Formula 1 or tapered structure element or single monomer unit
P: polymer of conjugated diene monomer, optionally with other monomers (except for diene compound of Formula 1)
X: polar group obtained by reacting living polymer chain with polar molecule
Y: mono- or diinitiator incorporated into polymer chain The above polymer structures can be obtained in the following fashion:

(1) Addition of the diene compound of Formula 1 to a mixture comprising conjugated diene monomer, optionally aromatic vinyl monomer, and initiator compound, as the polymerization proceeds, results in the provision of a statistical copolymer.

(1.1) In one preferred embodiment, the addition of the diene compound of Formula 1 is a continuous addition (during the polymerization process) or incremental addition (several dosing steps during the polymerization process).

(1.2) In another embodiment, all monomers including those of Formula 1 are added prior to the start of the polymerization process.

(2a) Dosing of diene compound of Formula 1 before addition of main amount of initiator a) together with main amounts of comonomers (tapered structure) or b) without other comonomers, which can be added after conversion of diene compound to generate block structure. After quantitative or close to quantitative conversion of monomers, a second addition of diene compound can be performed to generate block structure at polymer end. If A is a single monomer unit, the resulting structure is an alpha-omega-modified polymer.

(2b) Dosing of diene compound of Formula 1 before addition of main amount of initiator a) together with main amounts of comonomers (tapered structure) or b) without other comonomers, which can be added after conversion of diene compound to generate block structure. After quantitative or close to quantitative conversion of monomers, a chain end termination agent, such as for example an alkolol or water, is added. If A is a single monomer unit, the resulting structure is an alpha-modified polymer.

(2), (3) Dosing of diene compound of Formula 1 before addition of main amount of initiator a) together with main amounts of comonomers (tapered structure) or b) without other comonomers, which can be added after quantitative or close to quantitative conversion of diene compound to generate block structure. Additionally, several (n) dosing steps of diene compound of Formula 1 in variable proportions can be made at defined degrees of conversion of total monomer to generate n tapered or block structure elements within the polymer chain. After quantitative or close to quantitative conversion of monomers, a final addition of diene compound (2) or a chain-end modifying agent (as defined above) or coupling agent (as defined above) (3) can be used to generate block structure or another functionalization or coupling at polymer end.

(4) Several (n) dosing steps of diene compound of Formula 1 in variable proportions can be made at defined degrees of conversion of total monomer to generate n (tapered or block) structure elements within the polymer chain. After quantitative or close to quantitative conversion of monomers, a final addition of diene compound (2) or a chain-end modifying agent (as defined above) or coupling agent (as defined above) (3) can be used to generate block structure or another functionalization or coupling at polymer end.

(5) Dosing of diene compound of Formula 1 before addition of main amount of initiator a) together with main amounts of comonomers (tapered structure) or b) without other comonomers, which can be added after quantitative or close to quantitative conversion of diene compound to generate block structure. After quantitative or close to quantitative conversion of monomers, chain-end modifying agent (as defined above) or coupling agent (as defined above) can be added to functionalize or couple polymer chains.

Polymer

The elastomeric polymer according to the fourth aspect of the invention is obtainable by the process of the present invention, namely by polymerizing at least one conjugated diene monomer, a diene compound of Formula 1 and optionally one or more aromatic vinyl monomers in the presence of an initiator compound or a catalyst. The polymer of the invention may be a statistical, block or tapered copolymer, or an alpha- or alpha,omega-modified polymer where the diene compound of Formula 1 is incorporated in the polymer chain by means of one of its vinyl functions. The polymer may be linear or branched.

Specifically, the diene compound of Formula 1 may be incorporated in the polymer chain according to one or more of the following structures I, II, III, IV, V and VI:

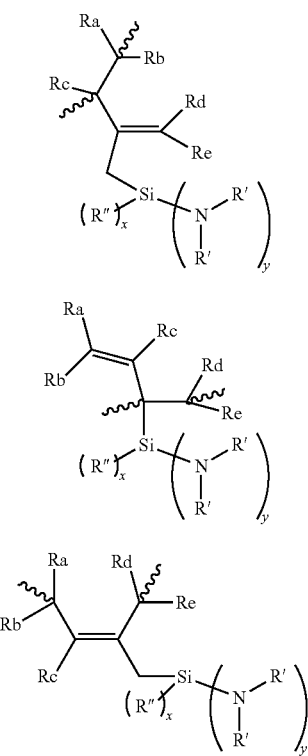

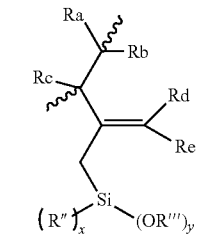

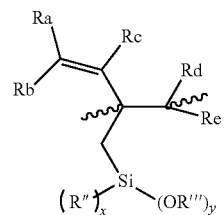

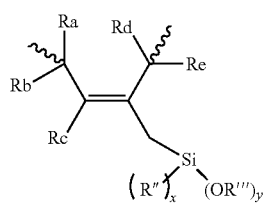

wherein $R_a$, $R_b$, $R_c$, $R_d$, $R_e$ R', R", x and y are as defined for the diene compound of Formula 1, or any of its embodiments, R''' is H or [Si], and ⁓ is the polymer backbone, wherein [Si] represents the chemical structure of one of formulae IV, V and VI such that the Si atom is shared by both structures. Structures IV, V, VI and the following structure VII, wherein R', R", x, y and ⁓ are as defined above, are examples of products obtained after aqueous (partial) protonolysis, e.g., after contact of the polymer with steam:

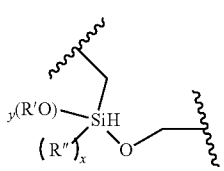

In preferred embodiments, the polymer of the invention is an SSBR (solution styrene butadiene rubber) with a preferred vinyl content of 15-85%, more preferably 30-75%, even more preferably 40-70% (dependent on the specific application), and a styrene content (depending on the specific application) of 40-70 wt. %, or 15-40 wt. %, or 2-15 wt. %; a PBR (polybutadiene rubber) with a vinyl content of <15%; or 15-40%, or 40-85%; a PIR (polyisoprene rubber); an SSIR (solution styrene isoprene rubber); or an SSIBR (solution styrene isoprene butadiene rubber); more preferably an SSBR or PBR; even more preferably an SSBR, each being modified by incorporation of the diene compound of Formula 1. In the case of an SSBR, the elastomeric polymer is characterized by a glass transition temperature (Tg, determined by DSC) of preferably −90 to 0° C., more preferably −80 to −5° C., even more preferably −70 to −10° C. The most preferred Tg for truck tire applications is −70 to −40° C., and the most preferred Tg for passenger car tire applications is −40 to −10° C.

In other preferred embodiments, the polymer of the invention is a BR (butadiene rubber) with a preferred vinyl content of <10%, more preferably <5%, and a cis content of >80% preferably >90%. In the case of a BR, the elastomeric polymer is characterized by a variable glass transition temperature (Tg, determined by DSC) depending on the concentration of compound shown by Formula 1 in the polymer. One preferred Tg range for high-cis BR is <−100° C.

Non-Cured Polymer Composition

The non-cured polymer composition of the fifth aspect of the present invention comprises the elastomeric polymer of the invention and one or more further components selected from (i) components which are added to or formed as a result of the polymerization process used for making said polymer and (ii) components which remain after solvent removal from the polymerization process. In particular, such components (i) and (ii) can be one or more components selected from oils (extender oils), fillers, stabilizers and further polymers (which are not the polymers of the invention). In one embodiment, the polymer composition additionally comprises one or more vulcanizing agents.

In one embodiment, the non-cured (non-crosslinked or unvulcanized) polymer composition is obtained by conventional work-up of the reaction mixture obtained in the polymerization process. Work-up means the removal of the solvent using steam stripping or vacuum evaporation techniques.

In another embodiment, the non-cured polymer composition of the invention is obtained as a result of a further mechanical mixing process involving the worked-up reaction mixture (including the polymer of the invention), preferably in the form of a rubber bale (i.e. the product of a conventional compounding process in an internal mixer and/or by means of a two-roll mill), and at least one filler. Further details are described in F. Röthemeyer, F. Sommer, Kautschuk Technologie: Werkstoffe-Verarbeitung-Produkte, 3rd ed., (Hanser Verlag, 2013) and references cited therein.

The following components are usually added in non-cured compositions used in tires: extender oils, stabilizers, fillers, further polymers.

(Extender) Oils

In one embodiment, the polymer composition of the present invention comprises the elastomeric polymer of the invention in combination with one or more oils, especially mineral oils. For representative examples and classification of oils see WO 2009/148932 and US 2005/0159513, the content of which is incorporated herein by reference in its entirety. Such oils include, for instance, conventionally known extender oils such as aromatic, naphthenic and paraffinic extender oils, for example MES (mild extraction solvate), TDAE (treated distillate aromatic extract), rubber-to-liquid (RTL) oils, biomass-to-liquid (BTL) oils, factices, extender resins or liquid polymers (such as liquid BR) having a median molecular weight (determined via GPC according to BS ISO 11344:2004) of from 500 to 20000 g/mol. When using a mineral oil as the extender oil, it is preferably one or more selected from DAE (Destillated Aromatic Extracts), RAE (Residual Aromatic Extract), TDAE, MES and naphthenic oils. The aforementioned oils comprise different concentrations of polycyclic aromatic compounds, parafinics, naphthenics and aromatics, and have different glass transition temperatures. The above mentioned types of oil have been characterized in "Kautschuk. Gummi Kunststoffe", vol. 52, pages 799-805. In some embodiments, MES, RAE and TDAE are preferred extender oils for rubber.

The one or more oils can be added to the polymer prior to or after the termination of the polymerization process. When the extender oil is added to the polymer solution, the timing of addition should preferably be after modification of the polymer or termination of the polymerization, for example after the addition of the modifying agent or polymerization termination agent. After the addition of extender oil, the oil-extended polymer composition can be obtained by separating any polymerization solvent from the polymer by means of a direct drying method or steam stripping, drying the rubber using a vacuum dryer, hot-air dryer, roller and the like.

The polymer composition may have contain one or more oils in a total amount of from 0 to 70 phr, preferably 0.1 to 60 phr, more preferably 0.1 to 50 phr. When liquid polymers are used as extender oils in the polymer composition of the present invention, they are not taken into account when calculating the composition of the polymer matrix.

In another embodiment, the oil is added to the "solvent-free" polymer in a mechanical mixer together with at least one filler, preferably with at least one filler and at least one further polymer.

Fillers

The polymer composition of the invention, which optionally comprises one or more extender oils as defined above, may further comprise one or more fillers. Filler can be added to the polymer prior to or after the termination of the polymerization process. Examples of suitable fillers include carbon black (including electroconductive carbon black), carbon nanotubes (CNT) (including discrete CNT, hollow carbon fibers (HCF) and modified CNT carrying one or more functional groups, such as hydroxyl, carboxyl and carbonyl groups), graphite, graphene (including discrete graphene platelets), silica, carbon-silica dual-phase filler, clays (layered silicates, including exfoliated nanoclay and organoclay), calcium carbonate, magnesium carbonate, magnesium oxide, titanium dioxide, rubber gels, lignin, amorphous fillers, such as glass particle-based fillers, starch-based fillers, and combinations thereof. Further examples of suitable fillers are described in WO 2009/148932, the content of which is incorporated herein by reference in its entirety.

Any type of carbon black conventionally known to a person of skill in the art may be used. In one embodiment, the carbon black has an iodine number according to ASTM D 1510 of 20 to 250 mg/g, preferably 30 to 180 mg/g, more preferably 40 to 180 mg/g, and even more preferably 40 to 130 mg/g, and a DBP number according to ASTM D 2414 of 80 to 200 ml/100 g, preferably 100 to 200 ml/100 g, more preferably 115 to 200 ml/100 g (the DBP number determines the specific absorption volume of carbon black or of any bright filler by means of dibutyl phthalate).

Any type of silica conventionally known to a person of skill in the art and suitable as filler for tire rubber blends may be used. It is particularly preferred to use highly dispersed, precipitated silica having an nitrogen surface area (BET surface area; according to DIN ISO 9277 and DIN 66132) of 35 to 350 m$^2$/g, preferably 35 to 260 m$^2$/g, more preferably 100 to 260 m$^2$/g and even more preferably 130 to 235 m$^2$/g, and having a CTAB surface area (according to ASTM D 3765) of 30 to 400 m$^2$/g, preferably 30 to 250 m$^2$/g, more preferably 100 to 250 m$^2$/g and even more preferably 125 to 230 m$^2$/g. Such silica results, e.g. in rubber blends for tire treads, to particularly beneficial physical properties of the vulcanizates. In addition, it may bring about advantages in the processing of the blend, namely by reducing the time required for blending, while maintaining product properties, thus improving productivity. Useful silicas include those of the type Ultrasil® VN3 (trademark of Evonik Industries) as well as highly dispersed types, so-called HD silicas (e.g. Zeosil® 1165 MP of Rhodia).

Stabilizers

One or more stabilizers ("antioxidants") can optionally be added to the polymer prior to or after the termination of the polymerization process to prevent the degradation of the elastomeric polymer by molecular oxygen. Antioxidants based on sterically hindered phenols, such as 2,6-di-tert-butyl-4-methylphenol, 6,6'-methylenebis(2-tert-butyl-4-methylphenol), Iso-octyl-3-(3,5-di-tert-butyl-4-hydroxyphenyl) propionate, hexamethylenebis [3-(3,5-di-tert-butyl-4-hydroxyphenyl)propionate], octadecyl-3-(3,5-di-tert-butyl-4-hydroxyphenyl) propionate, isotridecyl-3-(3,5-di-tert-butyl-4-hydroxyphenyl) propionate, 1,3,5-trimethyl-2,4,6-tris(3,5-di-tert-butyl-4-hydroxybenzyl) benzene, 2,2'-ethylidenebis-(4,6-di-tert-butylphenol), tetrakis [methylene-3-(3,5-di-tert-butyl-4-hydroxyphenyl)propionate]methane, 2-[1-(2-hydroxy-3, 5-di-tert-pentylphenyl)ethyl]-4, 6-di-tert-pentylphenyl acrylate and 2-tert-butyl-6-(3-tert-butyl-2-hydroxy-5-methylbenzyl)-4-methylphenyl acrylate, and antioxidants based on thio-esters, such as 4,6-bis(octylthiomethyl)-o-cresol and pentaerythrityl tetrakis(3-laurylthiopropionate), are typically used. Further examples of suitable stabilizers can be found in F. Rothemeyer, F. Sommer, Kautschuk Technologie, $2^{nd}$ ed., (Hanser Verlag, 2006) pages 340-344, and references cited therein.

Further Polymers

Apart from polymer of the invention, extender oil(s), filler(s), etc., the polymer composition of the invention may additionally contain further polymer, especially further elastomeric polymer. Further polymers may be added as solution to a solution of the inventive polymer prior to work up of the polymer blend or may be added during a mechanical mixing process, e.g. in a Brabender mixer.

Vulcanizing Agents and Vulcanizing Accelerators

The polymer composition of the invention may optionally further comprise one or more vulcanizing agents. Any vulcanizing agent conventionally used in the manufacture of rubber products can be used in the invention.

Sulfur, sulfur-containing compounds acting as sulfur donors such as dithiols, sulfur accelerator systems and peroxides are the most common vulcanizing agents. Examples of sulfur-containing compounds acting as sulfur donors include dithiodimorpholine (DTDM), tetramethylthiuram disulfide (TMTD), tetraethyl thiuram disulfide (TETD) and dipentamethylene thiuram tetrasulfide (DPTT). Examples of sulfur accelerators include amine derivates, guanidine derivates, aldehydeamine condensation products, thiazoles, xanthogenates, thiuram sulfides, dithiocarbamates and thiophosphates. It is preferably to use one or more sulfonamide accelerators selected from N-cyclohexyl 2-benzothiazol sulfenamide (CBS), N,N-dicyclohexyl benzothiazole 2-sulfenamide (DCBS), benzothiazyl 2-sulfenemorpholide (MBS) and N-tert-butyl 2-benzothiazyl sulfenamide (TBBS). Further crosslinking systems such as available under the trade names Vulkuren® (1,6-bis(N,N-dibenzyl thiocarbamoyldithio)-hexane; Lanxess), Duralink® or Perkalink® (1,3-bis(citraconimidomethyl)benzene; Lanxess) or disclosed in WO 2010/049261 may be added to the polymer composition. Examples of peroxides include di-tert.-butyl-peroxides, di-(tert.-butyl-peroxy-trimethyl-cyclohexane), di-(tert.-butyl-peroxy-isopropyl-)benzene, dichloro-benzoylperoxide, dicumylperoxides, tert.-butyl-cumyl-peroxide, dimethyl-di(tert.-butyl-peroxy)hexane, dimethyl-di(tert.-butyl-peroxy)hexine and butyl-di(tert.-butyl-peroxy)valerate (*Rubber Handbook, SGF, The Swedish Institution of Rubber Technolgy* 2000).

A vulcanizing accelerator of the sulfene amide-type, guanidine-type or thiuram-type can be used together with a vulcanizing agent as required.

In addition, the polymer composition of the invention may contain conventional additives and vulcanization auxiliaries in proportions conventionally used. Such additives include:

a) aging inhibitors such as N-phenyl N'-(1,3-dimethylbutyl)-p-phenylenediamine (6PPD), N,N'-diphenyl-p-phenylenediamine (DPPD), N,N'-ditolyl-p-phenylenediamine (DTPD), N-isopropyl N'-phenyl-p-phenylenediamine (IPPD), 2,2,4-trimethyl 1,2-dihydrochinolin (TMQ), b) activators such as zinc oxide and fatty acids (e.g. stearic acid), c) waxes, d) resins, especially adhesive resins, e) mastication additives such as 2,2'-dibenzamidodiphenyldisulfide (DBD) and f) processing additives such as zinc soaps and fatty acid esters and their derivatives.

Zinc oxide (zinc white) is preferably used as a component of the sulfur accelerator system.

A vulcanizing agent is typically added to the polymer composition in an amount of from 0.5 to 10 parts by weight or, in some embodiments, 1 to 6 parts by weight per 100 parts by weight of the total polymer. Examples of vulcanizing accelerators and amounts thereof added with respect to the total polymer are given in WO 2009/148932, the content of which is incorporated herein by reference in its entirety.

Vulcanized Polymer Composition

The vulcanized polymer composition of the sixth aspect of the invention is obtained by vulcanizing a polymer composition of the invention comprising one or more vulcanizing agents, under conditions and with machinery conventionally known in the art.

Article Comprising Vulcanized Polymer Composition

Since the vulcanized polymer compositions of the invention exhibit low rolling resistance, low dynamic heat buildup and increased wet grip, they are well suited for use in manufacturing, e.g., tires or parts of tires including for example: tire treads, side walls and tire carcasses as well as other industrial products such as belts, hoses, vibration dampers and footwear components. Thus, the article of the eighth aspect of the present invention comprises at least one component formed from the vulcanized polymer composition of the invention. The article may be, for instance, a tire, a tire tread, a tire side wall, a tire carcass, a belt, a gasket, a seal, a hose, a vibration damper, a golf ball or a footwear component, such as a shoe sole.

Definitions

Alkyl groups as defined herein, whether as such or in association with other groups, such as alkylaryl or alkoxy, include both straight chain alkyl groups, such as methyl (Me), ethyl (Et), n-propyl (Pr), n-butyl (Bu), n-pentyl, n-hexyl, etc., branched alkyl groups, such as isopropyl, tert-butyl, etc., and cyclic alkyl groups, such as cyclohexyl.

Aryl groups as defined herein include phenyl, biphenyl and other benzenoid compounds. Aryl groups preferably contain only one aromatic ring and most preferably contain a $C_6$ aromatic ring.

Alkylaryl groups as defined herein refer to a combination of one or more aryl groups bound to one or more alkyl groups, for example in the form of alkyl-aryl, aryl-alkyl, alkyl-aryl-alkyl and aryl-alkyl-aryl. Alkylaryl groups preferably contain only one aromatic ring and most preferably contain a $C_6$ aromatic ring.

The present invention will be explained in more detail by way of examples, which are not intended to be limiting the present invention.

EXAMPLES

Preparation of Aminosilane-Functionalized Diene Compound of Formula 1

Aminosilanes S1-S7 were prepared according to WO 2014/040640 using either (chloromethyl)dimethylchlorosilane or (chloromethyl)methyldichlorosilane and the required amine.

General Procedure for the Preparation of Aminosilanes S1-S7

A round-bottom flask was charged with cyclohexane, and 1.02 eq. of the corresponding amine and 1.1 eq. triethylamine were added. To this solution, 1 eq. (chloromethyl) dimethylchlorosilane or (chloromethyl)methyldichlorosilane was added dropwise under vigorous stirring. The mixture was stirred overnight, filtered to remove the precipitated ammonium salt and washed twice with cyclohexane. All volatiles were removed under reduced pressure to yield the corresponding amino silane product in quantitative yield. Analytical details for S1, S2 and S4 are found in WO 2014/040640. S3, S5, S6 and S7 are novel compounds, having the following analytical properties:

4-[(chloromethyl]dimethylsilyl)morpholine S3

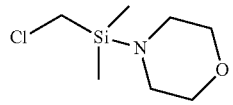

Chemical Formula: $C_7H_{16}ClNOSi$
Molecular Weight: 193,75

$^1$H NMR (400 MHz, 20° C., $C_6D_6$): δ=-0.03 [s, 6H, Si(CH$_3$)$_2$], 2.41 (s, 2H, CH$_2$Cl), 2.57 [t, J=4.8 Hz, 4H, N(CH$_2$)$_2$], 3.36 [t, J=4.8 Hz, 4H, O(CH$_2$)$_2$] ppm. $^{13}$C NMR (100 MHz, 20° C., $C_6D_6$): δ=-4.5 [Si(CH$_3$)$_2$], 30.2 (CH$_2$Cl), 45.6 [N(CH$_2$)$_2$], 68.5 [N(CH$_2$)$_2$] ppm.

1-[(chloromethyl]dimethylsilyl)-4-methylpiperazine S5

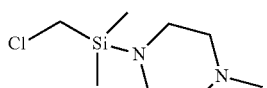

Chemical Formula: $C_8H_{19}ClN_2Si$
Molecular Weight: 206,79

$^1$H NMR (400 MHz, 20° C., $C_6D_6$): δ=0.05 [s, 6H, Si(CH$_3$)$_2$], 2.05, (s, 3H, NCH$_3$), 2.13 [t, J=4.9 Hz, 4H, N(CH$_2$)$_2$], 2.48 (s, 2H, CH$_2$Cl), 2.77 [t, J=4.8 Hz, 4H, N(CH$_2$)$_2$] ppm.
$^{13}$C NMR (100 MHz, 20° C., $C_6D_6$): δ=-4.2 [Si(CH$_3$)$_2$], 27.2 (CH$_2$Cl), 45.6 [N(CH$_3$)], 46.9 [N(CH$_2$)$_2$], 57.1 [N(CH$_2$)$_2$] ppm.

1-[(chloromethyl]dimethylsilyl)-4-ethylpiperazine S6

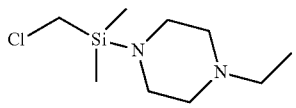

Chemical Formula: $C_9H_{21}ClN_2Si$
Molecular Weight: 220,82

$^1$H NMR (400 MHz, 20° C., $C_6D_6$): δ=0.06 [s, 6H, Si(CH$_3$)$_2$], 0.99 (t, J=7.1 Hz, 3, CH$_2$CH$_3$), 2.05, (br, 4H, N(CH$_2$)$_2$), 2.22 [t, J=7.1 Hz, 2H, CH$_2$CH$_3$], 2.49 (s, 2H, CH$_2$Cl), 2.79 [t, J=4.8 Hz, 4H, N(CH$_2$)$_2$] ppm.
$^{13}$C NMR (100 MHz, 20° C., $C_6D_6$): δ=-4.2 [Si(CH$_3$)$_2$], 12.3 (CH$_2$CH$_3$), 27.2 (CH$_2$Cl), 45.7 [N(CH$_2$)$_2$], 53.1 [N(CH$_2$CH$_3$)], 55.1 [N(CH$_2$)$_2$] ppm.

1-[(chloromethyl]dimethylsilyl)-4-benzylpiperazine S7

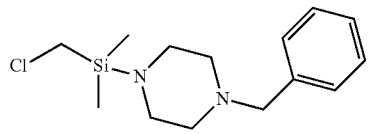

Chemical Formula: $C_{14}H_{23}ClN_2Si$
Molecular Weight: 282,89

$^1$H NMR (400 MHz, 20° C., $C_6D_6$): δ=0.03 [s, 6H, Si(CH$_3$)$_2$], 2.12, (br, 4H, N(CH$_2$)$_2$), 2.47 (s, 2H, CH$_2$Cl), 2.75 [t, J=4.7 Hz, 4H, N(CH$_2$)$_2$], 3.30 (s, 2H, CH$_2$Ar), 7.09-7.35 (m, 5H, Ar) ppm.
$^{13}$C NMR (100 MHz, 20° C., $C_6D_6$): δ=-4.3 [Si(CH$_3$)$_2$], 30.4 (CH$_2$Cl), 45.7 [N(CH$_2$)$_2$], 55.4 [N(CH$_2$)$_2$], 64.0 [CH$_2$Ar], 127.4 (Ar), 128.5 (Ar), 129.3 (Ar), 129.2 (Ar) ppm.

The diene MTMS used in Comparative Example 3 was prepared according to WO 2011/116223 starting from chloroprene and (chloromethyl)trimethylsilane.

The following aminosilane functionalized dienes were prepared according to a modified procedure from Sakurai et al. Tetrahedron 1983, 39, 883-894:

N,N-Diethyl-1,1-dimethyl-1-(2-methylenebut-3-en-1-yl)silanamine (M1)

Step 1:
Under inert conditions, freshly ground Mg turning (104 mmol) and a catalytic amount of dibromoethane and ZnCl$_2$ were charged with 44 mL THF into a round bottom flask and brought to reflux for 15 min. The temperature was then set to 55° C. and 1-(chloromethyl)-N,N-diethyl-1,1-dimethylsilanamine S1 (69 mmol) was added dropwise to the reaction mixture. The reaction mixture was then stirred for 3 h at 55° C. After this time, the reaction mixture was filtered under inert gas conditions and used as a solution in step 2.

Step 2:
Under inert gas conditions, freshly distilled chloroprene (46 mmol) was dissolved in 50 mL THF and 1,3-bis(diphenylphosphino)propane nickel(II) chloride (5 mol %) was added at rt. Then the solution prepared in step 1 was added dropwise and the reaction was stirred at rt overnight. The solvent was removed, the residue was then dissolved in cyclohexane and the salts were filtered off. The solvent of the remaining solution was again removed in vacuo. The crude product M1 was isolated by distillation (70° C., 1.5 mbar) in moderate yield (5.4 g, 60%) as a clear liquid.

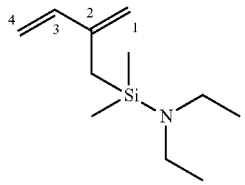

Chemical Formula: $C_{11}H_{23}NSi$
Molecular Weight: 197,40

Boiling point: 70° C. (1.5 mbar)

GC-MS (EI, 70 eV): m/z (%)=197 (M$^+$, 5), 182 (M$^+$-CH$_3$, 20), 155 (7), 130 (M$^+$-C$_6$H$_{16}$NSi, 100), 97 (5), 73 (20), 59 (80).

$^1$H NMR (400 MHz, 20° C., C$_6$D$_6$): δ=0.11 [s, 6H, Si(CH$_3$)$_2$], 0.93 (t, J=7.4 Hz, 6H, CH$_2$CH$_3$), 1.76 (s, 2H, CH$_2$), 2.72 (q, J=7.4 Hz, 4H, CH$_2$CH$_3$), 4.92 (m, 3H, 1-H, 4-H$_a$), 5.16 (m, 1H, 4-H$_b$), 6.36-6.42 (m, 1H, 3-H) ppm.

$^{13}$C NMR (100 MHz, 20° C., C$_6$D$_6$): δ=−1.4 [Si(CH$_3$)$_2$], 16.3 (CH$_2$CH$_3$), 40.6 (CH$_2$CH$_3$), 113.5 (1-C), 114.7 (4-C), 140.6 (3-C), 144.7 (2-C) ppm.

N,N-Dibutyl-1,1-dimethyl-1-(2-methylenebut-3-en-1-yl)silanamine (M2)

Step 1:

Under inert conditions, freshly ground Mg turning (104 mmol) and a catalytic amount of dibromoethane and ZnCl$_2$ were charged with 44 mL THF into a round bottom flask and brought to reflux for 15 min. The temperature was then set to 55° C. and 1-(chloromethyl)-N,N-dibutyl-1,1-dimethylsilanamine S2 (69 mmol) was added dropwise to the reaction mixture. The reaction mixture was then stirred for 4 h at 55° C. After this time, the reaction mixture was filtered under inert gas conditions and used as a solution in step 2.

Step 2:

Under inert gas conditions, freshly distilled chloroprene (46 mmol) was dissolved in 50 mL THF and 1,3-bis(diphenylphosphino)propane nickel(II) chloride (5 mol %) was added at rt. Then the solution prepared in step 1 was added dropwise and the reaction was stirred at rt overnight. The solvent was removed, the residue was then dissolved in cyclohexane and the salts were filtered off. The solvent of the remaining solution was again removed in vacuo. The crude product M2 was isolated by distillation (80° C., 0.06 mbar) in moderate yield (6.9 g, 52%) as a clear liquid.

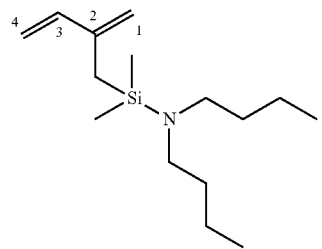

Chemical Formula: $C_{15}H_{31}NSi$
Molecular Weight: 253,51

Boiling point: 80° C. (0.06 mbar)

GC-MS (EI, 70 eV): m/z (%)=254 (M+H, 1), 238 (M$^+$-CH$_3$, 2), 210 (7), 130 (M$^+$-C$_3$H$_7$, 50), 186 (M$^+$-C$_{10}$H$_{24}$NSi), 100, 125(5), 97 (5), 59 (20).

$^1$H NMR (400 MHz, 20° C., C$_6$D$_6$): δ=0.16 [s, 6H, Si(CH$_3$)$_2$], 0.89 (t, J=7.3 Hz, 6H, CH$_2$CH$_3$), 1.11-1.26 (m, 4H, CH$_2$CH$_2$CH$_3$), 1.36-1.44 (m, 4H, CH$_2$CH$_2$CH$_3$), 1.82 (s, 2H, CH$_2$), 2.70 (t, 4H, J=7.3 Hz, CH$_2$CH$_2$CH$_3$), 4.90-5.03 (m, 3H, 1-H, 4-H$_a$), 5.16-5.22 (m, 1H, 4-H$_b$), 6.41 (dd, J=17.3, 7.2 Hz, 1H, 3-H) ppm.

$^{13}$C NMR (100 MHz, 20° C., C$_6$D$_6$): δ=−1.4 [Si(CH$_3$)$_2$], 14.4 (CH$_2$CH$_2$CH$_2$CH$_3$), 20.9 (CH$_2$CH$_2$CH$_2$CH$_3$), 32.9 (CH$_2$CH$_2$CH$_2$CH$_3$), 47.1 (CH$_2$CH$_2$CH$_2$CH$_3$), 113.6 (1-C), 114.8 (4-C), 140 (3-C), 144.7 (2-C) ppm.

4-[Dimethyl(2-methylenebut-3-en-1-yl)silyl]morpholine (M3)

Step 1:

Under inert conditions, freshly ground Mg turning (104 mmol) and a catalytic amount of dibromoethane and ZnCl$_2$ were charged with 44 mL THF into a round bottom flask and brought to reflux for 15 min. The temperature was then set to 55° C. and 4-((chloromethyl)-dimethylsilyl)morpholine S3 (69 mmol) was added dropwise to the reaction mixture. The reaction mixture was then stirred for 4 h at 55° C. After this time, the reaction mixture was filtered under inert gas conditions and used as a solution in step 2.

Step 2:

Under inert gas conditions, freshly distilled chloroprene (46 mmol) was dissolved in 50 mL THF and 1,3-bis(diphenylphosphino)propane nickel(II) chloride (5 mol %) was added at rt. Then the solution prepared in step 1 was added dropwise and the reaction was stirred at rt overnight. The solvent was removed, the residue was then dissolved in cyclohexane and the salts were filtered off. The solvent of the remaining solution was again removed in vacuo. The crude product M3 was isolated by distillation (70° C., 0.06 mbar) in moderate yield (5.8 g, 53%) as a clear liquid.

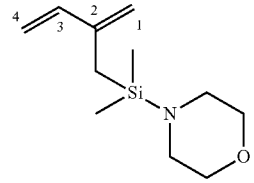

Chemical Formula: $C_{11}H_{21}NOSi$
Molecular Weight: 211,38

Boiling point: 70° C. (0.06 mbar)

GC-MS (EI, 70 eV): m/z (%)=211 (M$^+$, 55), 144 (M$^+$-SiMe$_2$NC$_4$H$_8$O, 100), 100 (15), 75 (15), 59 (50).

$^1$H NMR (400 MHz, 20° C., C$_6$D$_6$): δ=−0.01 [s, 6H, Si(CH$_3$)$_2$], 1.64 (s, 2H, CH$_2$), 2.62 [t, J=2.62 Hz, 4H, N(CH$_2$)$_2$], 3.43 [t, J=2.62 Hz, 4H, O(CH$_2$)$_2$], 4.83-4.99 (m, 3H, 1-H, 4-H$_a$), 5.08-5.13 (m, 1H, (m, 3H, 1-H), 6.37 (dd, J=17.2, 6.4 Hz, 1H, 3-H) ppm.

$^{13}$C NMR (100 MHz, 20° C., C$_6$D$_6$): δ=−2.5 [Si(CH$_3$)$_2$], 20.9 (CH$_2$Cl), 45.8 [N(CH$_2$)$_2$], 68.8 [O(CH$_2$)$_2$], 113.7 (1-C), 114.9 (4-C), 140.3 (3-C), 144.3 (2-C) ppm.

N,N,N',N'-Tetraethyl-1-methyl-1-(2-enebut-3-en-1-yl)silanediamine (M4)

Step 1:

Under inert conditions, freshly ground Mg turning (104 mmol) and a catalytic amount of dibromoethane and ZnCl$_2$ were charged with 44 mL THF into a round bottom flask and brought to reflux for 15 min. The temperature was then set to 55° C. and 1-(chloromethyl)-N,N,N',N'-tetraethyl-1-methylsilanediamine S4 (69 mmol) was added dropwise to the reaction mixture. The reaction mixture was then stirred for 4 h at 55° C. and then overnight at rt. After this time, the reaction mixture was filtered under inert gas conditions and used as a solution in step 2.

Step 2:

Under inert gas conditions, freshly distilled chloroprene (46 mmol) was dissolved in 50 mL THF and 1,3-bis(diphenylphosphino)propane nickel (II) chloride (5 mol %) was added at rt. Then the solution prepared in step 1 was added dropwise and the reaction was stirred at rt overnight. The solvent was removed, the residue was then dissolved in cyclohexane and the salts were filtered off. The solvent of the remaining solution was again removed in vacuo. The crude product M4 was isolated by distillation (75° C., 0.06 mbar) in moderate yield (5.5 g, 47%) as a clear liquid.

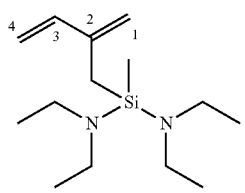

Chemical Formula: C$_{14}$H$_{30}$N$_2$Si
Molecular Weight: 254,49

Boiling point: 75° C. (0.06 mbar)

GC-MS (EI, 70 eV): m/z (%)=255 (M+H, 1), 239 (M$^+$-CH$_3$, 3), 187 (85), 116.1 (100), 72.1 (NEt$_2^+$, 5).

$^1$H NMR (400 MHz, 20° C., C$_6$D$_6$): δ=0.14 [s, 3H, Si(CH$_3$)], 0.97 (t, J=6.1 Hz, 12H, CH$_2$CH$_3$), 1.86 (s, 2H, CH$_2$), 2.80 (q, J=6.1 Hz, 8H, CH$_2$CH$_3$), 4.95-5.03 (m, 3H, 1-H, 4-H$_a$), 5.19-5.27 (m, 1H, 4-H$_b$), 6.43 (dd, J=17.6, 7.7 Hz, 1H, 3-H) ppm.

$^{13}$C NMR (100 MHz, 20° C., C$_6$D$_6$): δ=−2.7 [Si(CH$_3$)], 15.6 (CH$_2$CH$_3$), 39.5 (CH$_2$CH$_3$), 113.4 (1-C), 115.3 (4-C), 141.0 (3-C), 144.5 (2-C) ppm.

4-[Dimethyl(2-methylenebut-3-en-1-yl)silyl]-4-methylpiperazine (MS)

Step 1:

Under inert conditions, freshly ground Mg turning (104 mmol) and a catalytic amount of dibromoethane and ZnCl$_2$ were charged with 44 mL THF into a round bottom flask and brought to reflux for 15 min. The temperature was then set to 55° C. and 1-((chloromethyl)-dimethylsilyl)-4-methylpiperazine S5 (69 mmol) was added dropwise to the reaction mixture. The reaction mixture was then stirred for 15 h at 55° C. After this time, the reaction mixture was filtered under inert gas conditions and used as a solution in step 2.

Step 2:

Under inert gas conditions, freshly distilled chloroprene (46 mmol) was dissolved in 50 mL THF and 1,3-bis(diphenylphosphino)propane nickel (II) chloride (5 mol %) was added at rt. Then the solution prepared in step 1 was added dropwise and the reaction was stirred at rt overnight. The solvent was removed, the residue was then dissolved in cyclohexane and the salts were filtered off. The solvent of the remaining solution was again removed in vacuo. The crude product M5 was isolated by distillation (52° C., 0.001 mbar) in moderate yield (42%) as a clear liquid.

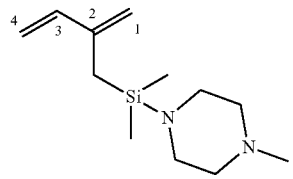

Chemical Formula: C$_{12}$H$_{24}$N$_2$Si
Molecular Weight: 224,42

Boiling point: 52° C. (0.001 mbar)

GC-MS (EI, 70 eV): m/z (%)=224.2 (M$^+$, 10), 157.1 (M$^+$-C$_7$H$_{17}$N$_2$Si, 100), 114.1 (15), 70.0 (30).

$^1$H NMR (400 MHz, 20° C., C$_6$D$_6$): δ=0.06 [s, 6H, Si(CH$_3$)$_2$], 1.71 (s, 2H, CH$_2$), 2.13, (br, 7H, N(CH$_2$)$_2$, NCH$_3$), 2.84 [t, J=4.8 Hz, 4H, N(CH$_2$)$_2$], 4.86-5.00 (m, 3H, 1-H, 4-H$_a$), 5.12-5.16 (m, 1H, 4-H$_b$), 6.38 (dd, J=17.2, 10.7 Hz, 1H, 3-H) ppm.

$^{13}$C NMR (100 MHz, 20° C., C$_6$D$_6$): δ=−2.1 [Si(CH$_3$)$_2$], 21.4 (CH$_2$Cl), 45.7 [N(CH$_2$)$_2$], 47.0 [N(CH$_3$)], 57.2 [N(CH$_2$)$_2$] 113.7 (1-C), 114.9 (4-C), 140.5 (3-C), 144.4 (2-C) ppm.

4-[Dimethyl(2-methylenebut-3-en-1-yl)silyl]-4-ethylpiperazine (M6)

Step 1:

Under inert conditions, freshly ground Mg turning (104 mmol) and a catalytic amount of dibromoethane and ZnCl$_2$ were charged with 44 mL THF into a round bottom flask and brought to reflux for 15 min. The temperature was then set to 55° C. and 1-((chloromethyl)-dimethylsilyl)-4-ethylpiperazine S6 (69 mmol) was added dropwise to the reaction mixture. The reaction mixture was then stirred for 15 h at 55° C. After this time, the reaction mixture was filtered under inert gas conditions and used as a solution in step 2.

Step 2:

Under inert gas conditions, freshly distilled chloroprene (46 mmol) was dissolved in 50 mL THF and 1,3-bis(diphenylphosphino)propane nickel (II) chloride (5 mol %) was added at rt. Then the solution prepared in step 1 was added dropwise and the reaction was stirred at rt overnight. The solvent was removed, the residue was then dissolved in cyclohexane and the salts were filtered off. The solvent of the remaining solution was again removed in vacuo. The crude product M6 was isolated by distillation (69° C., 0.01 mbar) in moderate yield (43%) as a clear liquid.

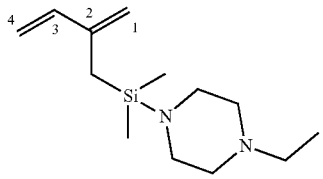

Chemical Formula: $C_{13}H_{26}N_2Si$
Molecular Weight: 238,45

Boiling point: 69° C. (0.01 mbar)
GC-MS (EI, 70 eV): m/z (%)=238.2 ($M^+$, 10), 171.1 ($M^+$-$C_8H_{19}N_2Si$, 100), 142.1 (10) 114.1 (12), 84.1 (25). 59.1 (10).
$^1$H NMR (400 MHz, 20° C., $C_6D_6$): δ=0.08 [s, 6H, Si(CH$_3$)$_2$], 1.01 (t, J=7.3 Hz, 2H, CH$_2$CH$_3$), 1.73 (s, 2H, CH$_2$), 2.18 (br, 4H, N(CH$_2$)$_2$), 2.25 (q, J=7.3 Hz, 2H, CH$_2$CH$_3$), 2.86 [t, J=4.8 Hz, 4H, N(CH$_2$)$_2$], 4.88-5.01 (m, 3H, 1-H, 4-H$_a$), 5.13-5.17 (m, 1H, 4-H$_b$), 6.39 (dd, J=17.3, 10.8 Hz, 1H, 3-H) ppm.
$^{13}$C NMR (100 MHz, 20° C., $C_6D_6$): δ=-2.2 [Si(CH$_3$)$_2$], 12.3 (CH$_2$CH$_3$), 21.4 (CH$_2$Cl), 45.8 [N(CH$_2$)$_2$], 53.3 [NCH$_2$CH$_3$)], 55.2 [N(CH$_2$)$_2$] 113.7 (1-C), 114.9 (4-C), 140.5 (3-C), 144.4 (2-C) ppm.

Polymerization
General Polymerization Procedure: Example A-D

Cyclohexane (amount given in Table 1), butadiene (97.8% of amount given in Table 1) and styrene (amount given in Table 1), TMEDA (amount given in Table 1) and functionalized diene M (amount and type of modifier is given in Table 1) were charged to an airfree 5 L reactor and the stirred mixture was heated up to 40° C. Then n-butyllithium was charged dropwise to react the impurities until the color of the reaction mixture changed to yellowish (titration). After that the recipe amount of initiator in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min. Then butadiene (0.5% of amount given in Table 1) was charged. After 5 min coupling agent Si (amount given in table) was added and the reaction was stirred for 20 min. Then another charge of butadiene (1.7% of amount given in Table 1) was added and after 5 min. stirring the chain-end modifier 2f (amount given in Table 1) was added. The reaction was terminated after 20 min with charge of methanol. The polymer solution was stabilized with Irganox 1520D, the polymer recovered by steam stripping and dried until a content of residual volatiles <0.6% was obtained. The complete data set of the sample is given in Table 1.

Comparative Example 1

Cyclohexane (2331.0 g), butadiene (321.0 g), styrene (87.1 g) and TMEDA (0.48 g) were charged to an airfree 5 L reactor and the stirred mixture was heated up to 40° C. Then n-butyllithium was charged dropwise to react the impurities until the color of the reaction mixture changed to yellowish (titration). After that the recipe amount of n-butyllithium (2.66 mmol) in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min. Then butadiene (2.8 g) was charged. After 5 min coupling agent Si (0.98 g, c=0.1467 mol/kg) was added and the reaction was stirred for 20 min. Then another charge of butadiene (6.8 g) was added and after 5 min. stirring the chainend modifier 2f (1.08 g, c=1.5804 mol/kg) was added. The reaction was terminated after 20 min with charge of methanol (0.6 g). The polymer solution was stabilized with Irganox 1520D (1.06 g), the polymer recovered by steam stripping and dried until a content of residual volatiles <0.6% was obtained. The complete data set of the sample is given in Table 1.

Comparative Example 2

Cyclohexane (2331.0 g), butadiene (316.7 g), styrene (86.0 g), isoprene (1.13 mmol) and TMEDA (0.47 g) were charged to an airfree 5 L reactor and the stirred mixture was heated up to 40° C. Then n-butyllithium was charged dropwise to react the impurities until the color of the reaction mixture changed to yellowish (titration). After that the recipe amount of n-butyllithium (2.75 mmol) in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min. Then butadiene (2.0 g) was charged. After 5 min coupling agent Si (0.96 g, c=0.1467 mol/kg) was added and the reaction was stirred for 20 min. Then another charge of butadiene (6.8 g) was added and after 5 min. stirring the chainend modifier 2f (1.15 g, c=1.5804 mol/kg) was added. The reaction was terminated after 20 min with charge of methanol (1.0 g). The polymer solution was stabilized with Irganox 1520D (1.06 g), the polymer recovered by steam stripping and dried until a content of residual volatiles <0.6% was obtained. The complete data set of the sample is given in Table 1.

Comparative Example 3

Cyclohexane (2348.6 g), butadiene (317.5 g), styrene (86.2 g), TMEDA (0.47 g) and functionalized diene MTMS (2.33 g) were charged to an airfree 5 L reactor and the stirred mixture was heated up to 40° C. Then n-butyllithium was charged dropwise to react the impurities until the color of the reaction mixture changed to yellowish (titration). After that the recipe amount of n-butyllithium (2.68 mmol) in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min. Then butadiene (1.9 g) was charged. After 5 min coupling agent Si (0.91 g, c=0.1467 mol/kg) was added and the reaction was stirred for 20 min. Then another charge of butadiene (5.5 g) was added and after 5 min. stirring the chainend modifier 2f (0.99 g, c=1.5804 mol/kg) was added. The reaction was terminated after 20 min with charge of methanol (1 g). The polymer solution was stabilized with Irganox 1520D (1.07 g), the polymer recovered by steam stripping and dried until a content of residual volatiles <0.6% was obtained. The complete data set of the sample is given in Table 1.

TABLE 1

Polymerization: Amount of substances per batch

|  | A | B | C | D | Comp. Ex. 1 | Comp. Ex. 2 | Comp. Ex. 3 |
|---|---|---|---|---|---|---|---|
| Cyclohexane [g] | 2328 | 2327 | 2325 | 2328 | 2331 | 2331 | 2348 |
| Butadiene [g] | 324.6 | 317.8 | 317.9 | 316.8 | 321.0 | 316.7 | 317.5 |
| Styrene [g] | 88.00 | 86.1 | 68.0 | 86.00 | 87.1 | 86.00 | 86.2 |
| TMEDA [mmol] | 4.535 | 4.037 | 4.042 | 4.087 | 4.117 | 4.037 | 4.039 |
| NB [mmol] | 2.5766 | 2.6480 | 2.8118 | 2.6549 | 2.6643 | 2.7454 | 2.6800 |
| modifier [g] | M1 3.70 | M2 4.21 | M3 3.51 | M4 4.23 | — | I 1.13 | MTMS 2.33 |
| Si [mmol] | 0.1590 | 0.1325 | 0.1319 | 0.1313 | 0.1441 | 0.1413 | 0.1339 |
| Cpd 2f [mmol] | 1.9402 | 1.8404 | 1.8213 | 1.6057 | 1.7693 | 1.3180 | 1.5635 |
| Mp [kg/mol] | 270 | 264 | 274 | 290 | 269 | 317 | 288 |
| Coupl. rate [%] | 14 | 16 | 17 | 21 | 18 | 22 | 32 |
| Vinyl content [%] | 63.0 | 59.4 | 62.2 | 60.8 | 62.6 | 60.9 | 61.2 |
| Styrene content [%] | 21.3 | 20.9 | 19.7 | 20.6 | 20.4 | 24.7 | 23.4 |
| Tg ° [C.] | −23 | −25 | −24 | −23 | −23 | −21 | −21 |
| $M_L$ [MU] | 47 | 49 | 42 | 109 | 44 | 68 | 61 |

NB = nBuLi,
M = functionalized diene,
I = Isoprene,
MTMS = Trimethyl(2-methylenebut-3-en-1-yl)silane,
Si = $SiCl_4$,
2f = 3-Methoxy-3,8,8,9,9-pentamethyl-2-oxa-7-thia-3,8-disiladecane General Polymerization Procedure Using Nd-Catalyst The homopolymerization of M4 was performed in a 20 ml screw cap glass vessels equipped with a magnetic stirrer. The vessel was charged with 0.5 g n-hexane and 0.2 g of M4 under inert gas conditions. Polymerization was initiated at room temperature by addition of 6 g of the catalyst solution prepared according to Table 2. The polymerization was terminated after 24 h by addition of 10 ml 4% Jonol/ethanole solution. The polymer E was obtained by filtration, dried at 80° C. for 4 h and analyzed by GPC.

TABLE 2

Conditions for Nd-catalyst formation

| Ingredient/reaction conditions | Amount |
|---|---|
| 1. Step | |
| n-Hexane [g] | 20 |
| 4.7384% DiBAH/n-Hexane solution [g] | 0.4 |
| 9.75% BD/n-Hexane solution [g] | 1.6227 |
| Aging at 20° C. [h] | 2 |
| 2. Step | |
| 0.5934% NdV/n-Hexane solution [g] | 0.073 |
| Aging at 20° C. [min] | 70 |
| 3. Step | |
| 1.067% EASC/n-Hexane solution | 0.025 |
| Aging at 20° C. [min] | 70 |

The catalyst formation is only one example. Other preformed Nd-catalyst systems may be used as well.

Formulation with Silica as Filler:

TABLE 3

Mixing recipe

| | [phr] |
|---|---|
| 1st mixing stage: | |
| SSBR-Polymer A-D | 80 |
| High cis 1,4-polybutadiene (Buna ™ cis 132-Schkopau, Trinseo Deutschland GmbH) | 20 |
| Precipitated silica (Silica 7000 GR, Evonik Industries) | 80 |
| Silane (Si 75, bis(triethoxysilylpropyl)disulfane, Evonik Industries) | 6.9 |
| Stearic acid (Cognis GmbH) | 1.0 |
| Antiozonant (Dusantox 6 PPD [N-(1,3-dimethylbutyl)-N'-phenyl-1,4-phenylenediamine], Duslo a.s.) | 2 |
| Zinc oxide (Grillo-Zinkoxid GmbH) | 2.5 |
| Ozone protecting wax (Antilux 654, Rhein Chemie Rheinau GmbH) | 1.5 |
| Softener (TDAE oil, VivaTec500, Hansen & Rosenthal KG) | 20 |
| 2nd mixing stage: mixing at 130° C. | all |
| 3rd mixing stage | |
| Sulfur (Solvay AG) | 2.1 |
| Accelerator (TBBS, N-tert-butyl-2-benzothiazolesulfenamide, Rhein Chemie Rheinau GmbH) | 1.9 |
| DPG (diphenylguanidine, Vulkacit D, Lanxess AG) | 1.9 |

TABLE 4

Compound information

|   | A | B | C | Comp. Ex. 1 | Comp. Ex. 2 | Comp. Ex. 3 |
|---|---|---|---|---|---|---|
| ML1 + 4 100° C. unmassed | 47 | 49 | 42 | 44 | 68 | 61 |
| CML1 + 4 | 116 | 119 | 102 | 69 | 80 | 71 |
| CML-ML | 69 | 60 | 60 | 25 | 12 | 10 |
| Tensile strength/MPa | 16 | 15 | 15 | 18 | 18 | 18 |
| Tan δ −10° C. | 0.787 | 0.719 | 0.714 | 0.665 | 0.740 | 0.713 |
| Tan δ 0° C. | 0.467 | 0.407 | 0.360 | 0.403 | 0.475 | 0.490 |
| Tan δ 60° C. | 0.081 | 0.066 | 0.057 | 0.092 | 0.110 | 0.141 |

Tan δ at 60° C. and tan δ at 0° C. are predictors for the rolling resistance and the wet grip of a tire respectively. Lower values of tan δ at 60° C. correspond to a reduced rolling resistance of a tire and higher values of tan δ at 0° C. correspond to an improved wet grip property of a tire. The data in Table 4 show that the present invention leads to a significant decrease in tan δ values at 60° C. with up to 60% improvement compared to Comparative example 3, thus also showing, that the improvement is due to the monomer of Formula 1 of the invention, containing a functionalized aminosilane group, in the polymer. At the same time, wet grip indicator tan δ 0° C. can be kept on a similar level or is improved when compared with the comparative examples. Hence, the use of the polymers of the invention, comprising the monomers of Formula 1 of the invention, results in a reduced rolling resistance of the tire, at a similar or improved wet grip performance.

Test Methods

The molecular weight analyses were carried out by SEC/RI using a HEWLETT PACKARD HP 1100. The eluent THF was degassed on line. The solvent flow rate was 1.0 ml/min. 100 L of polymer solution were injected per analysis. The analyses were carried out at 40° C. The molecular weights were initially calculated based on a polystyrene calibration and given in the tables as polystyrene. The real molecular weights (SSBR molecular weights) can be determined dividing by a factor derived from an earlier comparison between molecular weights from SEC/RI and SEC/MALLS. The value of the factor depends on the polymer composition (styrene and butadiene content). A factor of 1.52 can be used for SSBR with 21% and 30% styrene. A factor of 1.84 can be used for SBR with 0% styrene. A factor of 1.56 can be used for SSBR with 16% styrene. A factor of 1.41 can be used for SSBR with 45% styrene.

NMR-spectroscopy was performed on a BRUKER Avance 400 in a 5 mm BBO probe. Solvents, frequencies and temperature are given in the characterization data.

FTIR-spectroscopy measured in attenuated total reflection was used to determine the vinyl content and styrene content.

The glass transition temperature was determined using the DSC Q2000 under the following conditions:
Weight: ca. 10-12 mg
Sample container: Alu/S
Temperature range: (−140 . . . 80) ° C.
Heating rate: 20 K/min respectively 5 K/min
Cooling rate: free cooling
Purge gas: 20 ml Ar/min
Cooling agent: liquid nitrogen
Each sample was measured at least once. The measurements contain two heating runs. The 2nd heating run was used to determine the glass transition temperature.

Measurements of non-vulcanized rheological properties according to ASTM D 5289-95 were made using a rotor-less shear rheometer (MDR 2000 E) to characterize cure characteristics.

Test pieces were vulcanized by t95 at 160° C., especially for hardness tests the specimen were vulcanized by T95+5 min at 160° C. Dynamic properties as tan δ at 0° C. and 60° C. were measured using dynamic spectrometer Eplexor 150N/500N manufactured by Gabo Qualimeter Testanlagen GmbH (Germany) applying a compression dynamic strain of 0.2% at a frequency of 2 Hz. Heat build-up was measured according to ASTM D 623, method A, on a Doli 'Goodrich'-Flexometer.

EMBODIMENTS

The present invention, as generally described above, specifically relates to the following embodiments:

1. A diene compound of the following Formula 1:

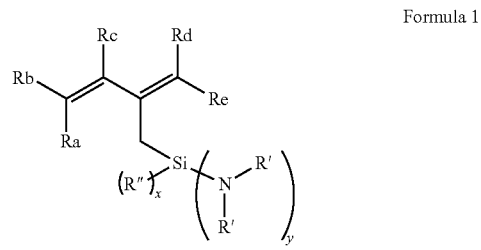

Formula 1 wherein
each R' is independently selected from $C_1$-$C_{12}$ alkyl, $C_6$-$C_{18}$ aryl, $C_7$-$C_{18}$ alkylaryl, tri($C_1$-$C_6$ alkyl, $C_6$-$C_{12}$ aryl or $C_7$-$C_{18}$ alkylaryl)silyl and allyl, wherein two R' groups may be connected to form a ring and the ring may contain, further to the Si-bonded nitrogen atom, one or more of an oxygen atom, a nitrogen atom, an >N($C_1$-$C_6$ alkyl or $C_7$-$C_{18}$ alkylaryl) group and a sulfur atom;

each R" is independently selected from $C_1$-$C_6$ hydrocarbyl;

$R_a$, $R_b$, $R_c$, $R_d$ and $R_e$ are independently selected from hydrogen, methyl and ethyl;

x is an integer selected from 0, 1 and 2, y is an integer selected from 1, 2 and 3 and x+y=3.

2. The diene compound according to item 1, wherein each of $R_a$, $R_b$, $R_c$, $R_d$ and $R_e$ is hydrogen and x and y are independently integers selected from 1 and 2.

3. The diene compound according to item 1 and 2, wherein R" is methyl.

4. A process for preparing the diene compound of Formula 1 as defined in any one of items 1 to 3, said process comprising reacting a compound of Formula 2 and a compound of Formula 3 in the presence of (i) a metal selected from the group consisting of magnesium, zinc, aluminum and boron and (ii) a transition metal catalyst in a solvent:

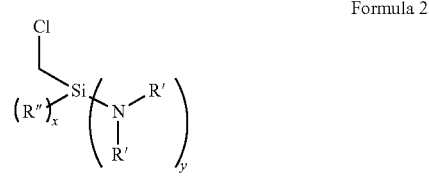

Formula 2

Formula 3

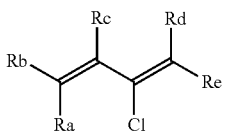

wherein $R_a$, $R_b$, $R_c$, $R_d$, $R_e$ R', R", x and y are as defined in any one of items 1 to 5.

5. A process for preparing an elastomeric polymer, said process comprising the step of polymerizing at least one conjugated diene monomer, a diene compound of Formula 1 as defined in any one of items 1 to 3 and optionally one or more aromatic vinyl monomers in the presence of an initiator compound or a catalyst to form a living elastomeric polymer.

6. The process according to item 5, further comprising reacting the living elastomeric polymer with one or more agents selected from coupling agents and chain end-modifying agents.

7. The process according to item 5 or 6, wherein the initiator compound is an organometallic compound with the metal of the organometallic compound being selected from lithium, sodium and potassium.

8. The process according to item 5 or 6, wherein the catalyst contains one or more selected from nickel, cobalt, titanium and rare earth elements having an atomic number of 57 to 71 in the periodic table, preferably selected from lanthanum, praseodymium, neodymium, gadolinium and dysprosium, more preferably neodymium.

9. An elastomeric polymer obtainable by the process as defined in any one of items 5 to 8.

10. The elastomeric polymer according to item 9, which contains one or more of the following chemical structures I, II, III, IV, V and VI:

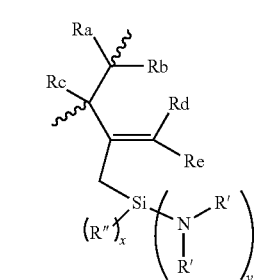

I

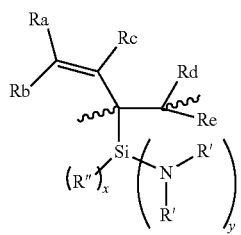

II

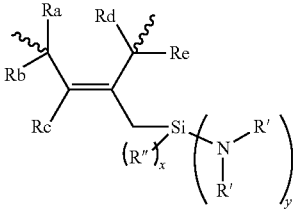

III

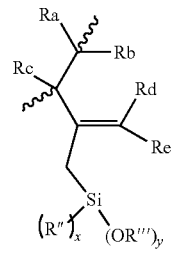

IV

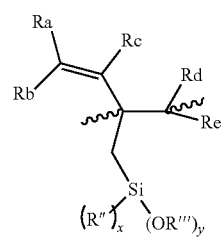

V

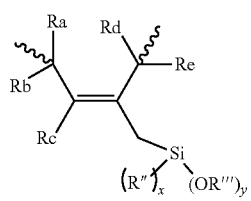

VI wherein $R_a$, $R_b$, $R_c$, $R_d$, $R_e$ R', R", x and y are as defined as in any one of items 1 to 5, R''' is H or [Si], and ⌇ is the polymer backbone, wherein [Si] represents the chemical structure of one of formulae IV, V and VI such that the Si atom is shared by both structures.

11. A non-cured polymer composition comprising an elastomeric polymer as defined in item 9 or 10 and one or more further components selected from (i) components which are added to or formed as a result of the polymerization process used for making said polymer, (ii) components which remain after solvent removal from the polymerization process and (iii) components which are added to the polymer after completion of the polymer manufacturing process.

12. The polymer composition according to item 11, further comprising one or more vulcanizing agents.

13. A vulcanized polymer composition obtainable by vulcanizing the polymer composition as defined in item 12.

14. A method of making a vulcanized polymer composition, comprising the step of vulcanizing the polymer composition as defined in item 12.

15. An article comprising at least one component formed from the vulcanized polymer composition as defined in item 13.

The invention claimed is:

1. A diene compound of the following Formula 1:

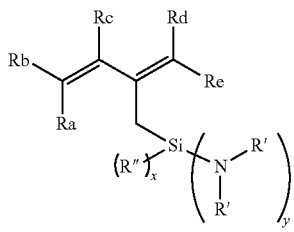

Formula 1 wherein
- each R' is independently selected from $C_1$-$C_{12}$ alkyl, $C_6$-$C_{18}$ aryl, $C_7$-$C_{18}$ alkylaryl, tri($C_1$-$C_6$ alkyl, $C_6$-$C_{12}$ aryl or $C_7$-$C_{18}$ alkylaryl)silyl and allyl, wherein two R' groups may be connected to form a ring and the ring may contain, further to the Si-bonded nitrogen atom, one or more of an oxygen atom, a nitrogen atom, an >N($C_1$-$C_6$ alkyl or $C_7$-$C_{18}$ alkylaryl) group, or a sulfur atom;
- each R" is independently selected from $C_1$-$C_6$ hydrocarbyl;
- $R_a$, $R_b$, $R_c$, $R_d$, and $R_e$ are independently selected from hydrogen, methyl, and ethyl;
- x is an integer selected from 0, 1, and 2,
- y is an integer selected from 1, 2, and 3 and
- x+y=3.

2. The diene compound according to claim 1, wherein each of $R_a$, $R_b$, $R_c$, $R_d$, and $R_e$ is hydrogen and x and y are independently integers selected from 1 and 2.

3. The diene compound according to claim 1, wherein R" is methyl.

4. The diene compound according to claim 1, wherein R' is selected from methyl, ethyl, n-butyl, n-hexyl, n-octyl, cyclohexyl, or benzyl.

5. The diene compound according to claim 1, wherein y is 1 and the group —(NR'R')$_y$ is represented by piperazine, optionally substituted at the nitrogen atom in position 4 with $C_1$-$C_6$ alkyl or $C_7$-$C_{18}$ alkylaryl, piperidine, or morpholine.

6. A process for preparing the diene compound of Formula 1 as defined in claim 1, the process comprising reacting a compound of Formula 2 and a compound of Formula 3 in the presence of (i) a metal selected from the group consisting of magnesium, zinc, aluminum, and boron and (ii) a transition metal catalyst in a solvent:

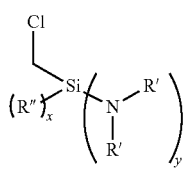

Formula 2

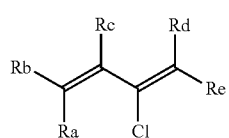

Formula 3 wherein $R_a$, $R_b$, $R_c$, $R_d$, $R_e$, R', R", x, and y are as defined in claim 1.

7. A process for preparing an elastomeric polymer, the process comprising the step of polymerizing at least one conjugated diene monomer, a diene compound of Formula 1 as defined in claim 1 and, optionally one or more aromatic vinyl monomers in the presence of an initiator compound or a catalyst to form a living elastomeric polymer.

8. The process according to claim 7, further comprising reacting the living elastomeric polymer with one or more agents selected from coupling agents or chain end-modifying agents.

9. The process according to claim 8 wherein the chain end-modifying agent is one or more selected from sulfanylsilane compounds, aminosilane compounds, epoxysilane compounds, or siloxane compounds.

10. The process according to claim 7, wherein the initiator compound is an organometallic compound with the metal of the organometallic compound being selected from lithium, sodium, and potassium.

11. The process according to claim 7, wherein the catalyst contains one or more selected from nickel, cobalt, titanium, or rare earth elements having an atomic number of 57 to 71 in the periodic table.

12. An elastomeric polymer obtain by the process as defined in claim 7.

13. The elastomeric polymer according to claim 12, which contains one or more of the following chemical structures I, II, III, IV, V, and VI:

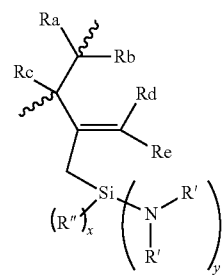

I

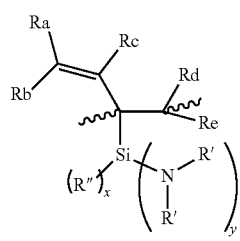

II

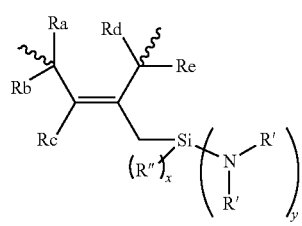

III

-continued

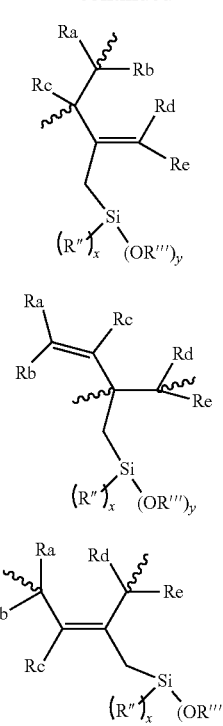

wherein $R_a$, $R_b$, $R_c$, $R_d$, $R_e$, R', R", x, and y are as defined as in claim 1, R''' is H or [Si], and ⁓ is the polymer backbone, wherein [Si] represents the chemical structure of one of formulae IV, V, and VI such that the Si atom is shared by both structures.

14. A non-cured polymer composition comprising an elastomeric polymer as defined in claim 12 and one or more further components selected from (i) components which are added to or formed as a result of the polymerization process used for making the polymer, (ii) components which remain after solvent removal from the polymerization process, or (iii) components which are added to the polymer after completion of the polymer manufacturing process.

15. The polymer composition according to claim 14, further comprising one or more components selected from extender oils, stabilizers, or further polymers.

16. The polymer composition according to claim 14, further comprising one or more fillers, wherein the one or more fillers are selected from carbon black, carbon nanotubes, graphite, graphene, silica, or carbon-silica dual-phase filler.

17. The polymer composition according to claim 14, further comprising one or more vulcanizing agents.

18. A vulcanized polymer composition obtained by vulcanizing the polymer composition as defined in claim 17.

19. An article comprising at least one component formed from the vulcanized polymer composition as defined in claim 18.

20. A method of making a vulcanized polymer composition, comprising the step of vulcanizing the polymer composition as defined in claim 17.

* * * * *